United States Patent
Kim et al.

(10) Patent No.: US 8,323,466 B2
(45) Date of Patent: Dec. 4, 2012

(54) MICROFLUIDIC-BASED LAB-ON-A-TEST CARD FOR A POINT-OF-CARE ANALYZER

(75) Inventors: Sunnie Park Kim, Manhattan Beach, CA (US); Young Shik Shin, Pasadena, CA (US); Changgeng Liu, Alhambra, CA (US); Rory Kelly, Escalon, CA (US); Becky Chan, Los Angeles, CA (US)

(73) Assignee: NanoIVD, Inc., Los Angeles, CA (US)

( * ) Notice: Subject to any disclaimer, the term of this patent is extended or adjusted under 35 U.S.C. 154(b) by 368 days.

(21) Appl. No.: 12/632,661

(22) Filed: Dec. 7, 2009

(65) Prior Publication Data

US 2010/0140110 A1    Jun. 10, 2010

Related U.S. Application Data

(60) Provisional application No. 61/120,253, filed on Dec. 5, 2008.

(51) Int. Cl.
*H01L 51/10* (2006.01)
*H01L 51/30* (2006.01)
*G01N 27/00* (2006.01)

(52) U.S. Cl. ........... 204/403.01; 257/20; 257/40; 435/4; 435/6.1; 977/702; 977/734; 977/938

(58) Field of Classification Search .................. 204/450, 204/403.01; 435/6.1, 4; 977/702, 734, 938; 257/20, 40
See application file for complete search history.

(56) References Cited

U.S. PATENT DOCUMENTS

| | | | |
|---|---|---|---|
| 7,301,199 B2 | 11/2007 | Lieber et al. | |
| 7,385,267 B2 | 6/2008 | Lieber et al. | |
| 7,410,904 B2 | 8/2008 | Stasiak et al. | |
| 7,553,453 B2 | 6/2009 | Gu et al. | |
| 7,575,681 B2 | 8/2009 | Angelescu et al. | |
| 2002/0117659 A1* | 8/2002 | Lieber et al. | 257/14 |
| 2008/0283875 A1* | 11/2008 | Mukasa et al. | 257/253 |
| 2009/0104689 A1 | 4/2009 | Kim et al. | |
| 2009/0152597 A1 | 6/2009 | Kim et al. | |
| 2009/0152598 A1 | 6/2009 | Baek et al. | |
| 2010/0128260 A1* | 5/2010 | Afzali-Ardakani et al. | 356/213 |

FOREIGN PATENT DOCUMENTS

WO    WO2006/134942    * 12/2006

OTHER PUBLICATIONS

Wang et al. (Small 2007, 3, No. 8, 1350-1355).*
Fournie GJ, Martres F, Pourrat JP, Alary C, Rumeau M. Plasma DNA as cell death marker in elderly patients. Gerontology, 1993, pp. 215-221, vol. 39, No. 4, Karger, Basel.

(Continued)

*Primary Examiner* — Jeffrey T Barton
*Assistant Examiner* — Jennifer Dieterle

(57) ABSTRACT

A microfluidic-based lab-on-a-test card is described. The test card is used with a point-of-care (POC) analyzer. The test card is designed to receive a sample and then, with the use of the POC analyzer, quantify or count a particular substance in the sample. The test card may be comprised of multiple layers. In one embodiment, the test card includes a primary separation chamber with a filtration surface, a trapping channel, and a particle detector. The test card may also include a nanowire sensor.

14 Claims, 11 Drawing Sheets

OTHER PUBLICATIONS

Leon SA, Shapiro B, Sklaroff DM, Yaros MJ. Free DNA in the serum of cancer patients and the effect of therapy. Cancer Research, Mar. 1977, pp. 646-650, vol. 37, No. 3, American Association for Cancer Research, Philadelphia.

Bret L, Lule J, Pourrat JP, Fournie GJ. Extracellular DNA in blood and urine as a potential marker for cytotoxicity and nephrotoxicity in the mouse. Renal Failure, 1990, pp. 133-139, vol. 12, No. 3, Marcel Dekker, New York.

Ishizawa M, Kobayashi Y, Miyamura T, Matsuura S. Simple procedure of DNA isolation from human serum. Nucleic Acids Research, Oct. 25, 1991, p. 5792, vol. 19, No. 20, Oxford University Press, Oxford.

Chen XQ, Stroun M, Magnenat J-L, Nicod LP, Kurt A-M, Lyautey J, Lederrey C, Anker, P. Microsatellite alterations in plasma DNA of small cell lung cancer patients. Nature Medicine, Sep. 1996, pp. 1033-1035, vol. 2, No. 9, Nature Publishing Group, London.

Stroun M, Anker P, Maurice P, Lyautey J, Lederrey C, Beljanski M. Neoplastic characteristics of the DNA found in the plasma of cancer patients. Oncology, 1989, pp. 318-322, vol. 46, No. 5, Karger, Basel.

Sorenson GD, Pribish DM, Valone FH, Memoli VA, Bzik DJ, Yao S-L. Soluble normal and mutated DNA sequences from single-copy genes in human blood. Cancer Epidemiology, Biomarkers & Prevention, Jan./Feb. 1994, pp. 67-71, vol. 3, No. 1, American Association for Cancer Research, Philadelphia.

Vasioukhin V, Anker P, Maurice P, Lyautey J, Lederrey C, Stroun M. Point mutations of the N-ras gene in the blood plasma DNA of patients with myelodysplastic syndrome or acute myelogenous leukaemia. British Journal of Haematology, Apr. 1994, pp. 774-779, vol. 86, No. 4, Wiley, Hoboken.

Maire F, Micard S, Hammel P, Voitot H, Levy P, Cugnenc P-H, Ruszniewski P, Laurent Puig P. Differential diagnosis between chronic pancreatitis and pancreatic cancer: value of the detection of KRAS2 mutations in circulating DNA. British Journal of Cancer, Aug. 27, 2002, pp. 551-554, vol. 87, No. 5, Nature Publishing Group, London.

Yamada T, Nakamori S, Ohzato H, Oshima S, Aoki T, Higaki N, Sugimoto K, Akagi K, Fujiwara Y, Nishisho I, Sakon M, Gotoh M, Monden M. Detection of K-ras gene mutations in plasma DNA of patients with pancreatic adenocarcinoma: correlation with clinicopathological features. Clinical Cancer Research, Jun. 1998, pp. 1527-1532, vol. 4, No. 6, American Association for Cancer Research, Philadelphia.

Tsang JCH, Lo YMD. Circulating nucleic acids in plasma/serum. Pathology, Apr. 2007, pp. 197-207, vol. 39, No. 2, Informa, London.

Daniels JS, Pourmand N. Label-free impedance biosensors: opportunities and challenges. Electroanalysis, 2007, pp. 1239-1257, vol. 19, No. 12, Wiley-VCH, Weinheim.

Patolsky F, Zheng G, Lieber CM. Nanowire-based biosensors. Analytical Chemistry, Jul. 1, 2006, pp. 4261-4269, vol. 78, No. 13, ACS Publications, Washington DC.

Bunimovich YL, Shin YS, Yeo W-S, Amori M, Kwong G, Heath JR. Quantitative real-time measurements of DNA hybridization with alkylated nonoxidized silicon nanowires in electrolyte solution. Journal of the American Chemical Society, Dec. 20, 2006, pp. 16323-16331, vol. 128, No. 50, ACS Publications, Washington DC.

Patolsky F, Zheng G, Hayden O, Lakadamyali M, Zhuang X, Lieber CM. Electrical detection of single viruses. Proceedings of the National Academy of Sciences, Sep. 28, 2004, pp. 14017-14022, vol. 101, No. 39, National Academy of Sciences, Washington DC.

Wang WU, Chen C, Lin K-H, Fang Y, Lieber CM. Label-free detection of small-molecule-protein interactions by using nanowire nanosensors. Proceedings of the National Academy of Sciences, Mar. 1, 2005, pp. 3208-3212, vol. 102, No. 9, National Academy of Sciences, Washington DC.

Zheng G, Patolsky F, Cui Y, Wang WU, Lieber CM. Multiplexed electrical detection of cancer markers with nanowire sensor arrays. Nature Biotechnology, Oct. 2005, pp. 1294-1301, vol. 23, No. 10, Nature Publishing Group, London.

Stern E, Klemic JF, Routenberg DA, Wyrembak PN, Turner-Evans DB, Hamilton AD, Lavan DA, Fahmy TM, Reed MA. Label-free immunodetection with CMOS-compatible semiconducting nanowires. Nature, Feb. 1, 2007, pp. 519-522, vol. 445, No. 7127, Nature Publishing Group, London.

Stern N, Wagner R, Sigworth FJ, Breaker R, Fahmy TM, Reed MA. Importance of the Debye screening length on nanowire field effect transistor sensors. Nano Letters, Oct. 3, 2007, pp. 3405-3409, vol. 7, No. 11, ACS Publications, Washington DC.

Hruban RH, Goggins M, Parsons J, Kern SE. Progression model for pancreatic cancer. Clinical Cancer Research, Aug. 2000, pp. 2969-2972, vol. 6, No. 8, American Association for Cancer Research, Philadelphia.

Salbe C, Trevisiol C, Ferruzzi E, Mancuso T, Nascimbeni R, Di Fabio F, Salerni B, Dittadi R. Molecular detection of codon 12 K-RAS mutations in circulating DNA from serum of colorectal cancer patients. The International Journal of Biological Markers, 2000, pp. 300-307, vol. 15, No. 4, Wichtig Editore, Milano.

Abou-Alfa GK, O'Reilly EM, Schwartz GK, Kelsen DP, Jacobs G, Capanu M, Chapman PB. Vaccination of pancreatic cancer patients against mutated K-ras. 2006 Gastrointestinal Cancers Symposium, abstract No. 122, American Society of Clinical Oncology.

Wang J, Palecek E, Nielsen PE, Rivas G, Cai X, Shiraishi H, Dontha N, Luo D, Farias Pam. Peptide nucleic acid probes for sequence-specific DNA biosensors. Journal of the American Chemical Society, Aug. 21, 1996, pp. 7667-7670, vol. 118, No. 33, ACS Publications, Washington DC.

Briones C, Mateo-Marti E, Gomez-Navarro C, Parro V, Roman E, Martin-Gago JA. Ordered self-assembled monolayers of peptide nucleic acids with DNA recognition capability. Physical Review Letters, Nov. 12, 2004, pp. 208103-1 to 208103-4, vol. 93, No. 20, American Physical Society, Ridge, NY.

Lui Yyn, Chik K-W, Chiu RWK, Ho C-Y, Lam CWK, Lo YMD. Predominant hematopoietic origin of cell-free DNA in plasma and serum after sex-mismatched bone marrow transplantation. Clinical Chemistry, 2002, pp. 421-427, vol. 48, No. 3, American Association for Clinical Chemistry, Washington DC.

Lee T-H, Montalvo L, Chrebtow V, Busch MP. Quantitation of genomic DNA in plasma and serum samples: higher concentrations of genomic DNA found in serum than in plasma. Transfusion, Feb. 2001, pp. 276-282, vol. 41, No. 2, Wiley, Hoboken.

Jung M, Klotzek S, Lewandowski M, Fleischhacker M, Jung K. Changes in concentration of DNA in serum and plasma during storage of blood samples. Clinical Chemistry, Jun. 1, 2003, pp. 1028-1029, vol. 49, No. 6, American Association for Clinical Chemistry, Washington DC.

Lam NYL, Rainer TH, Chiu RWK, Lo, YMD. EDTA is a better anticoagulant than heparin or citrate for delayed blood processing for plasma DNA analysis. Clinical Chemistry, Jan. 1, 2004, pp. 256-257, vol. 50, No. 1, American Association for Clinical Chemistry, Washington DC.

Vogelstein B, Gillespie D. Preparative and analytical purification of DNA from agarose. Proceedings of the National Academy of Sciences, Feb. 1979, pp. 615-619, vol. 76, No. 2, National Academy of Sciences, Washington DC.

Gao Z, Agarwal A, Trigg, AD, Singh N, Fang C, Tung C-H, Fan Y, Buddharaju KD, Kong J. Silicon nanowire arrays for label-free detection of DNA. Analytical Chemistry, May 1, 2007, pp. 3291-3297, vol. 79, No. 9, ACS Publications, Washington DC.

Wang D, Sheriff BA, Heath JR. Silicon p-FETs from ultrahigh density nanowire arrays. Nano Letters, May 2, 2006, pp. 1096-1100, vol. 6, No. 6, ACS Publications, Washington DC.

Fritz J, Cooper EB, Gaudet S, Sorger PK, Manalis SR. Electronic detection of DNA by its intrinsic molecular charge. Proceedings of the National Academy of Sciences, Oct. 29, 2002, pp. 14142-14146, vol. 99, No. 22, National Academy of Sciences, Washington DC.

\* cited by examiner

SEQUENCE LISTING

```
<160> NUMBER OF SEQ ID NOS: 6

<210> SEQ ID NO 1
<211> LENGTH: 60
<212> TYPE: DNA
<213> ORGANISM: Unknown
<220> FEATURE:
<223> OTHER INFORMATION: Description of Unknown:
      K-RAS sequence

<400> SEQUENCE: 1
atgactgaat ataaacttgt ggtagttgga gctggtggcg taggcaagag tgccttgacg    60

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
```

-continued

```
atgactgaat ataaacttgt ggtagttgga gctcgtggcg taggcaagag tgccttgacg     60

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atgactgaat ataaacttgt ggtagttgga gctgatggcg taggcaagag tgccttgacg     60

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atgactgaat ataaacttgt ggtagttgga gctgttggcg taggcaagag tgccttgacg     60

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atgactgaat ataaacttgt ggtagttgga gcttgtggcg taggcaagag tgccttgacg     60

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atgactgaat ataaacttgt ggtagttgga gctggtgacg taggcaagag tgccttgacg     60
```

MICROFLUIDIC-BASED LAB-ON-A-TEST CARD FOR A POINT-OF-CARE ANALYZER

CROSS-REFERENCE TO RELATED APPLICATION

This application claims the benefit of U.S. provisional patent application Ser. No. 61/120,253, entitled "INTEGRATED SEMICONDUCTOR-NANOSENSOR ANALYSIS SYSTEM," filed Dec. 5, 2008.

BACKGROUND

The detection with antibodies, proteins, peptides, nucleic acids, aptamers, and cell receptors of certain cell types or substances in biological samples such as blood, urine, and other bodily fluids is used in the diagnosis of disease, the assessment of the efficacy of treatments, and many other purposes. Where current diagnostic assays require a patient visit a physician or travel to a laboratory, point-of-care assays may be conducted by the primary care physician in their office or by the patient in their home as well as by health care workers in remote geographical locations or in hospitals for bed-ridden patients.

Microfluidic techniques have been applied in an attempt to address some of the disadvantages of conventional laboratory techniques. For example, microfluidic techniques require much smaller quantities of reagents. However, microfluidic techniques are often able to handle biological samples of much smaller volumes, which may limit sensitivity when the quantity of the particular cells or substances to be detected are very rare or minute in amount.

What is needed is a system and method for detecting a particular substance in a biological sample that is inexpensive and not labor intensive.

What is needed is a system and method for detecting a particular substance in a biological sample that can give rapid results at the point of care.

What is needed is a system and method for detecting a particular substance in a biological sample that is very sensitive.

DETAILED DESCRIPTION OF PREFERRED EMBODIMENTS

Figure 1A:
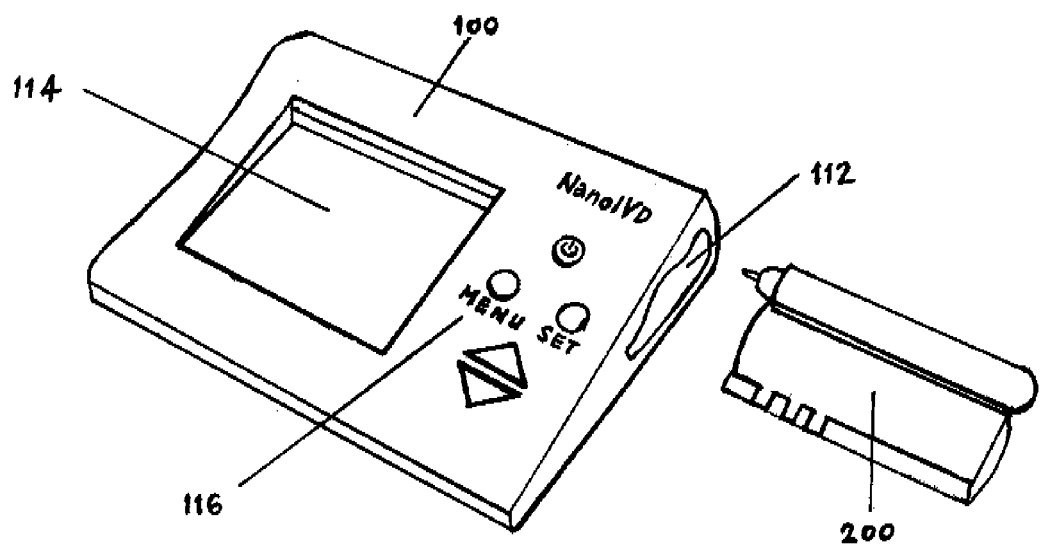
FIGS. 1A-1B show one embodiment of a point-of-care (POC) analyzer suitable for use with a test card.
Figure 1B:
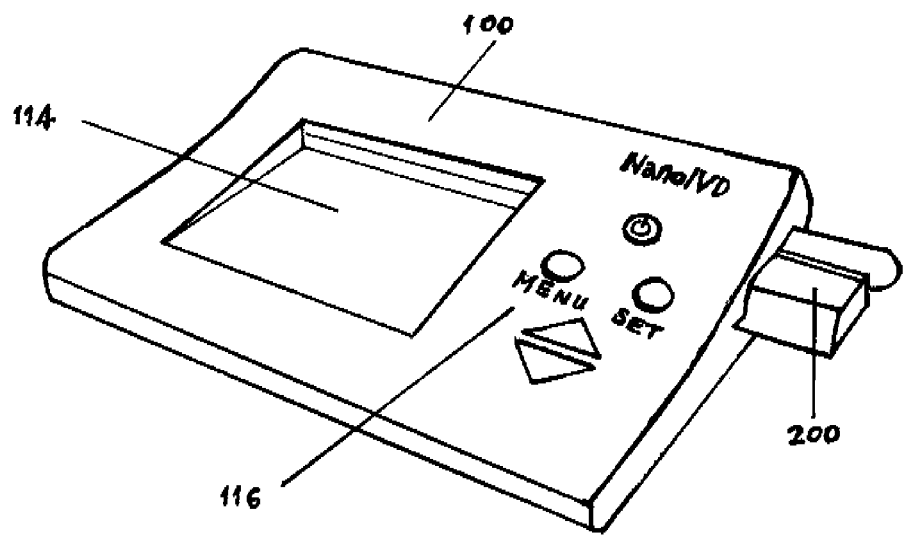

FIGS. 1A-1B show one embodiment of a point-of-care (POC) analyzer 100 suitable for use with a test card 200. POC analyzer 100 includes a card slot 112, display 114, and controls 116. Card slot 112 is configured to receive test card 200. Display 114 shows the status of POC analyzer 100 and test results. Controls 116 turn POC analyzer 100 on and off, starts and stops testing, and changes display 114.

POC analyzer 100 includes a pressure device, such as a syringe, peristaltic pump, or any other suitable pump, for applying pressure to test card 200. POC analyzer 100 also includes electrical contacts configured to mate with corresponding electrical contacts on test card 200.

Test card 200 is designed to receive a sample and then, with the use of POC analyzer 100, quantify or count a particular substance in the sample. The sample may be whole blood, plasma, serum, fine needle aspirate, bone marrow sample, spinal fluid, cyst fluid, joint or synovial fluid, endometrial aspiration sample, gastric sample, ocular fluid, ovarian fluid, tissue cultured media, urine, or other biological or non-biological sample.

In one embodiment, test card 200 is configured to receive a sample of whole blood and provide an approximate count of the number of circulating tumor cells (CTCs) in the sample. In the same embodiment or in other embodiments, test card 200 may be used to provide an approximate count of the number of white blood cells in the sample lacking any of the CD45, CD14, CD33, CD16, CD24, CD64, or CD15 cell surface markers. In the same embodiment or in yet other embodiments, test card 200 may be used to provide an approximate count of cells with specific surface markers, such as epidermal growth factor receptor (EGFR) amplification for cancer cells, CD133 for cancer stem cells, or T-cell receptor for antigen specificity.

Test card 200 may be made of plastic, glass, or any other suitable material. Test card 200 may be constructed of one or more layers. The layers may be coupled together using epoxy, thermal bonding, or any other suitable method and/or materials. Test card 200 may have dimensions of approximately 70 mm×55 mm×5 mm. Test card 200 may be packaged with a buffer supply, and may have electrical contacts arranged to facilitate access.

Figure 2A:
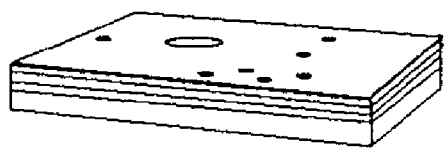
FIGS. 2A-2B show assembled and exploded views of one embodiment of a test card.
Figure 2B:
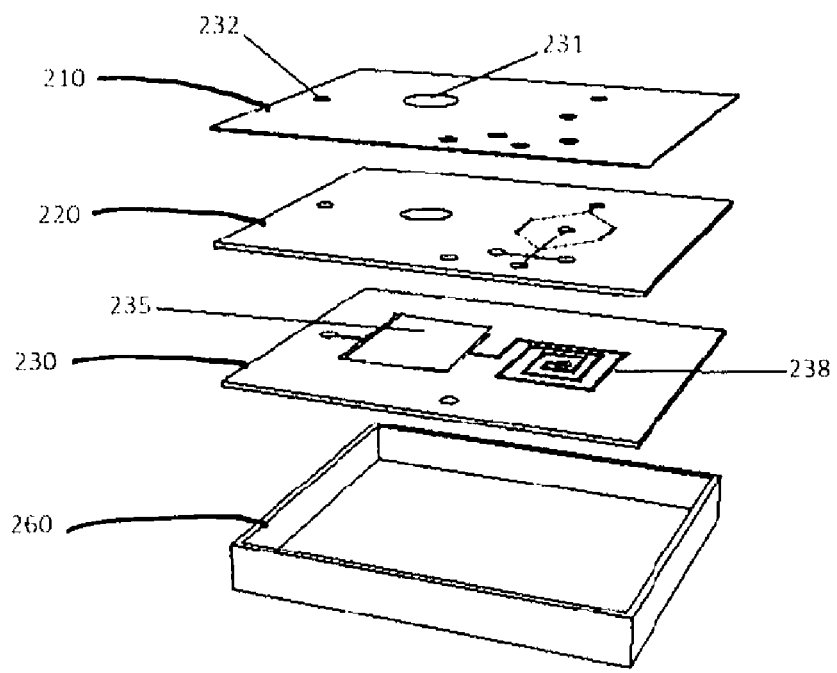

FIGS. 2A-2B show assembled and exploded views of one embodiment of test card 200. Test card 200 is suitable for receiving a sample of whole blood and providing an approximate count of CTCs. Test card 200 is made up of a stack of layers including a top layer 210, a particle detector layer 220, a primary separation layer 230, and a waste collection layer 260. The functionality of these layers may be combined or split into fewer layers or more layers, depending on manufacturing and cost considerations.

Primary separation layer 230 includes a sample inlet 231. Sample inlet 231 is capable of receiving a large sample of approximately 0.01 ml to 10 ml. Sample inlet 231 is of a size which minimizes the chances of clogging. Sample inlet 231 may have a diameter of approximately 0.5 mm to 10 mm, and preferably approximately 5 mm. Sample inlet 231 may pass through top layer 210 and particle detector layer 220 to reach primary separation layer 230.

Primary separation layer 230 also includes a primary separation chamber 235 in fluid communication with sample inlet 231. Primary separation layer 230 may also include a trapping channel 238 in fluid communication with primary separation chamber 235.

Figure 3A:
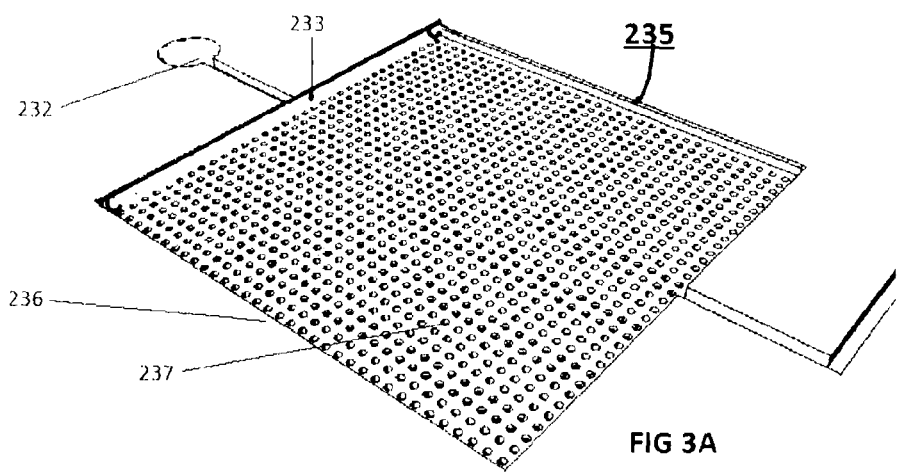
FIG. 3A shows an enlarged view of a primary separation chamber.
Figure 3B:
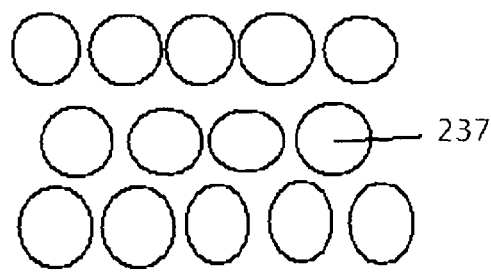
FIG. 3B shows an enlarged view of pores.

FIG. 3A shows an enlarged view of primary separation chamber 235. Primary separation chamber 235 includes a filtration surface 236. Filtration surface 236 includes a plurality of pores 237 of suitable size. For detecting CTCs in whole blood, pores 237 have a size which prevent CTCs and larger white blood cells from passing through, while allowing smaller white blood cells, red blood cells, platelets, plasma, and other blood components to pass through, or a diameter of approximately 1 μm to 30 μm, and preferably approximately 16 μm. For other applications, such as detecting cancer cell antigens, nucleic acids, antibodies, immunoglobulins, other biomarkers, and microbes, pores 237 may have a diameter of approximately 1 μm. Filtration surface 236 may have a porosity greater than 50%. Porosity refers to the portion or percentage of filtration surface 236 that is made up of pores 237. FIG. 3B shows an enlarged view of pores 237. Pores 237 may be arranged in a hexagonal, rectangular, or any other suitable fashion. Pores 237 may be round, hexagonal, or any other suitable shape. Pores 237 may be of a uniform size or of different sizes. Filtration surface 236 may be approximately 6 mm long by 6 mm wide, and may include approximately 100,000 pores.

Sample inlet 231 is positioned over filtration surface 236. Sample inlet 231 directs a sample of whole blood into primary separation chamber 235 from above filtration surface 236, and causes the sample to flow in a direction substantially perpendicular to filtration surface 236. This has the effect of increasing the flow rate and decreasing test time.

Primary separation layer 230 also includes a buffer inlet 232 in fluid communication with primary separation chamber 235. Buffer inlet 232 may pass through top layer 210 and particle detector layer 220 to reach primary separation layer 230. Buffer inlet 232 may be in fluid communication with a pressure device in POC analyzer 100. Buffer inlet 232 directs buffer into primary separation chamber 235 in a direction substantially parallel to filtration surface 236 to create a "sweeping" action across filtration surface 236 and toward trapping channel 238. Buffer inlet 232 may first introduce buffer into a buffer trough 233 which extends across substantially an entire side of filtration surface 236. Buffer fills buffer trough 233 and then overflows onto filtration surface 236. Buffer trough 233 may have a top that is positioned at approximately the same level as filtration surface 236. Alternatively, buffer inlet 232 may include a buffer diffuser which spreads buffer across substantially an entire side of filtration surface 236. Buffer inlet 232 directs buffer across filtration surface 236 and causes a sweeping of filtration surface 236 as buffer flows from buffer inlet 232 towards trapping channel 238.

Filtration surface 236 may be formed as part of primary separation layer 230, or may be manufactured separately and then coupled to primary separation layer 230. Filtration surface 236 may be manufactured by injection molding, microlithography, micromachining techniques such as photoimaging, wet and dry etching, radiation based processing such as radiation "unzipping," and laser ablation. "Wet etching" generally refers to etching by contact with liquid elements. "Dry etching" generally refers to etching by contact with gas or plasma. With laser ablation, each pulse of laser light removes a small portion of polymeric material. Synchotrons deliver highly directional x-ray radiation that can be used to unbond or "unzip" the polymer backbone of acrylic material, such as polymethyl methacrylate (PMMA). Using this concept, exposed areas of a polymer membrane, as defined by an X-ray mask having absorbing and transmitting sections defining the desired pattern, may be "unzipped" by ionizing radiation and subsequently developed away by solvent bath.

For counting CTCs, sensitivity corresponds to sample volume, because the number of CTCs per volume is very small. Test card 200 is capable of filtering a blood sample having a volume of up to 10 ml or more. This sample size may be 10 times greater than the sample sizes typically encountered in microfluidics devices. Consequently, this large sample size results in a sensitivity that may be 10 times greater.

Figure 4A:
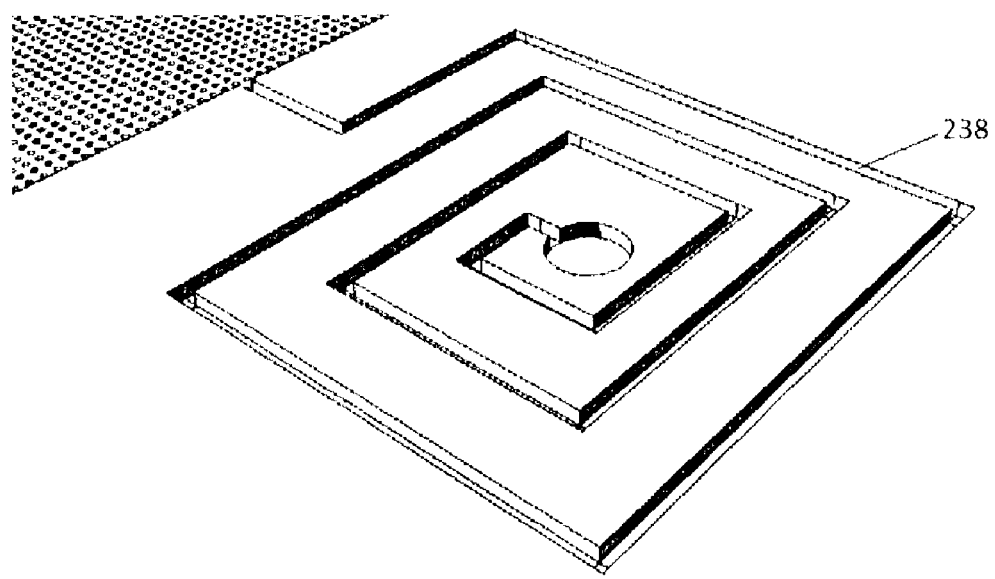
FIGS. 4A-4B show perspective and cross-sectional views of one embodiment of a trapping channel 238
Figure 4B:
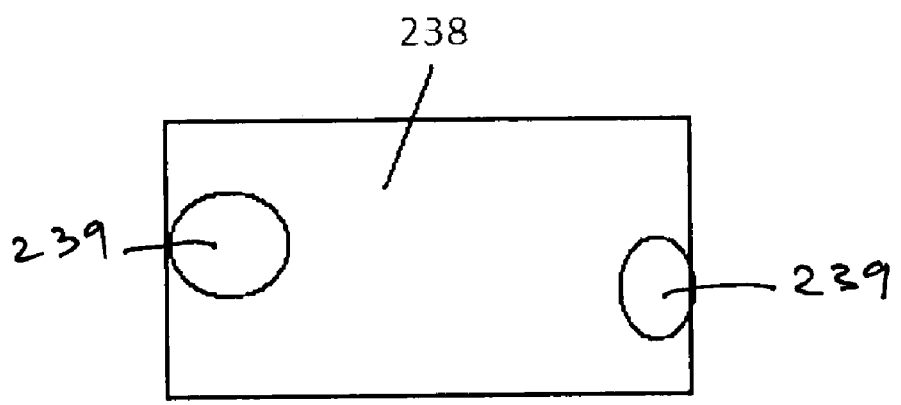

FIGS. 4A-4B show perspective and cross-sectional views of one embodiment of trapping channel 238. Trapping channel 238 includes walls that are treated with a binding agent that will selectively bind a specifically targeted component in the sample. In one embodiment, trapping channel 238 has walls that are treated with CD45 antibodies that will bind with white blood cells. In other embodiments, trapping channel 238 has walls that may be treated with antibodies, aptamers, peptides, and/or small molecules which can selectively bind unwanted components. Trapping channel 238 is wide enough such that it will not clog as white blood cells or other blood components 239 bind to its walls. Trapping channel 238 may have a width of approximately 20 μm to 1000 μm, and preferably approximately 400 μm. Trapping channel 238 is also long enough to enhance the trapping of the white blood cells or other blood component. Trapping channel 238 may have a total path length of approximately 0.1 cm to 10 cm, and preferably approximately 5 cm. Trapping channel 238 describes a meandering path which enhances the trapping of the white blood cells or other blood component. In the embodiment shown, trapping channel 238 describes a spiral-like path with several turns of approximately 90 degrees, which causes the white blood cells or other blood component to come into contact with the walls. These turns also create turbulence when particles collide into the walls from direct path of its flow and with other particles, causing increased frequency of contact with the walls. Trapping channel 238 may have a cross-sectional shape that is square, rectangular, triangular, or any other suitable shape.

Particle detector layer 220 includes a particle detector 300 in fluid communication with trapping channel 238. Particle detector 300 is capable of quantifying the amount of a particular substance or counting the number of cells in the sample. Particle detector 300 may be an agar-based salt bridge impedance sensor, a DADMAC salt bridge impedance sensor, or any other suitable sensor.

Figure 5A:
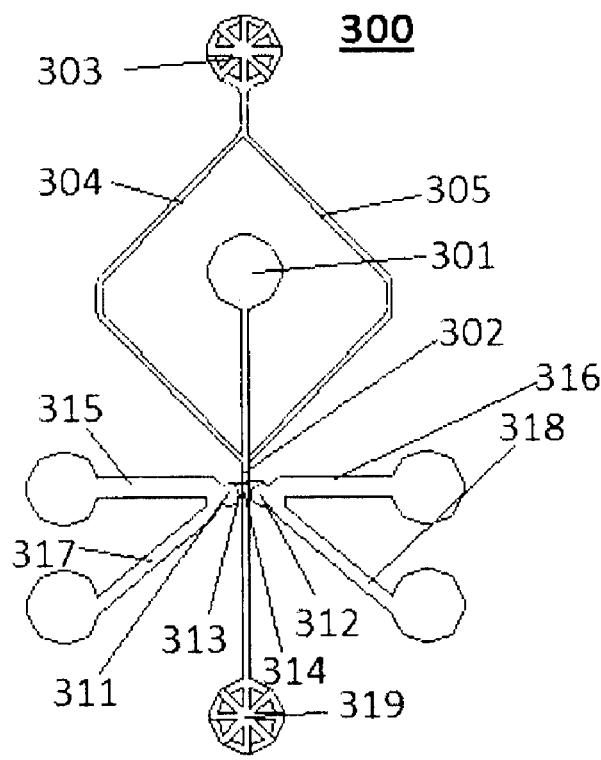
FIGS. 5A-5B show enlarged views of one embodiment of a particle detector.
Figure 5B:
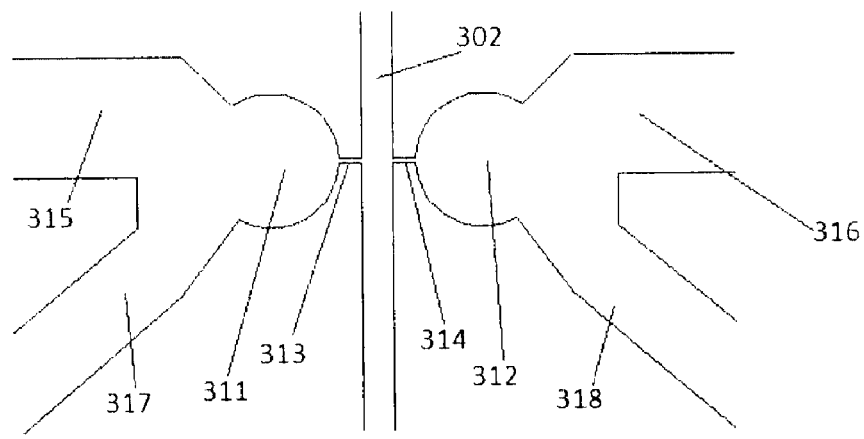

FIGS. 5A-5B show enlarged views of one embodiment of particle detector 300. Particle detector 300 is a salt bridge impedance sensor, specifically an agar-based salt bridge impedance sensor. Particle detector 300 includes a sensor inlet 301 which receives the sample from trapping channel 238 and directs it into a main flow channel 302. Main flow channel 302 may have a width of approximately 0.05 mm to 0.5 mm, and preferably approximately 0.1 mm. Particle detector 300 may also include a buffer reservoir 303 and buffer introduction channels 304 and 305 which introduce buffer on both sides of main flow channel 302. Buffer introduction channels 304 and 305 hydrodynamically focus the sample in the center of main flow channel 302. This arranges the cells or particles in the sample in substantially a single line. Alternatively, a single buffer introduction channel may be used to hydrodynamically focus the sample on one side of main flow channel 302.

Particle detector 300 also includes salt bridge chambers 311 and 312 which contain agar and are coupled to main flow channel 302 via connection channels 313 and 314. Connection channels 313 and 314 may have a width of approximately 0.001 mm to 0.05 mm, and a length of approximately 0.01 mm to 0.2 mm, and preferably approximately 0.01 mm wide and 0.1 mm long. Electrolyte inlets 315 and 316 contain electrolyte and are in fluid communication with salt bridge chambers 311 and 312. Electrolyte inlets 315 and 316 are coupled to electrodes 325 and 326. Electrodes 325 and 326 pass through top layer 210 and may be electrically coupled to POC analyzer 100. Electrodes 325 and 326 may be made of Ag/AgCl any other suitable material. A collection chamber 319 in fluid communication with main flow channel 302 collects the sample at the end.

Particle detector 300 may include agar inlets 317 and 318 which facilitate the manufacture of salt bridge chambers 311 and 312. Salt bridge chambers 311 and 312 may be manufactured by filling agar inlets 317 and 318 with an agar mixture of approximately 2-10% agar and 1M KCl (weight by volume). This agar mixture is heated up until the agar is fully dissolved. The agar mixture becomes clear when it is ready, and is introduced into agar inlets 317 and 318 immediately when ready. The agar mixture may be introduced into agar inlets 317 and 318 by capillary force or positive pressure. The agar mixture will fill agar inlets 317 and 318 and salt bridge chambers 311 and 312 first. Connection channels 313 and 314 are narrow and the high flow resistance will prevent the agar mixture from running into main flow channel 302. The size of connection channels 313 and 314 allows for more consistent filling of agar or other polymer in the channels due to the small volume used. This makes it less likely to have differentially polymerized salt bridge if filling more polymer as would be in case of larger connection channels. This may lead to greater reproducibility of test results. Once salt bridge chambers 311 and 312 are filled with the agar mixture, the flow can be stopped. Particle detector 300 can be stored at room temperature until the agar mixture has cooled down and solidified. Particle detector 300 may be used at this time after a 1M KCl solution is introduced into electrolyte inlets 315 and 316. The manufacture of an agar-based salt bridge sensor does not require photolithography. The manufacture of an agar-based salt bridge sensor is compatible with a wide range of materials, including soft materials such as polydimethylsiloxane (PDMS). The manufacture of the agar-based salt bridge sensor does not require UV as a photoinitiator, and cross linker.

Figure 5C:
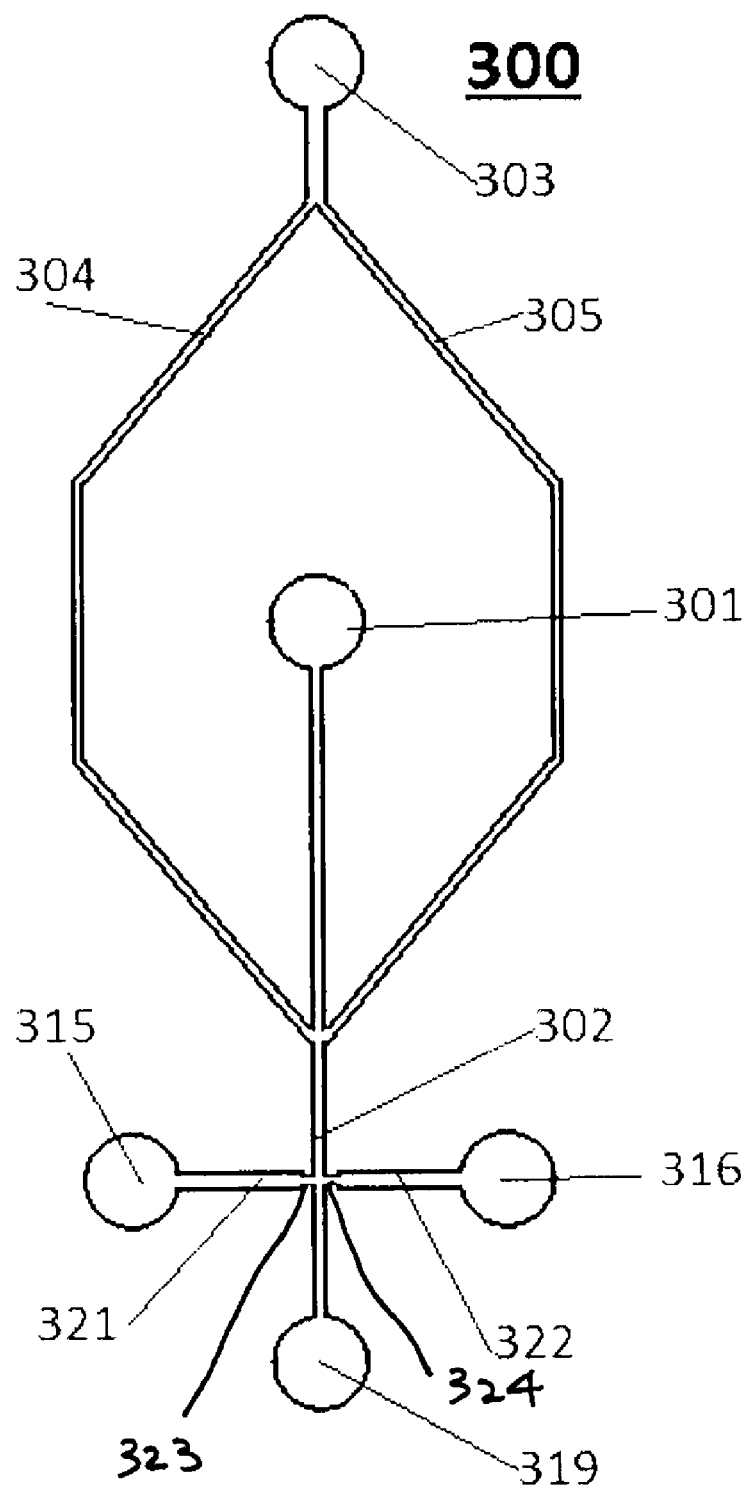
FIG. 5C shows an enlarged view of another embodiment of a particle detector.

FIG. 5C shows an enlarged view of another embodiment of a particle detector 300. Particle detector 300 is a salt bridge impedance sensor, specifically a diallyldimethylammonium chloride (DADMAC) salt bridge sensor. Particle detector 300 includes a sensor inlet 301 which receives the sample from trapping channel 238 and directs it into a main flow channel 302. Main flow channel 302 may have a width of approximately 0.05 mm to 0.5 mm, and preferably approximately 0.1 mm. Particle detector 300 may also include a buffer reservoir 303 and buffer introduction channels 304 and 305 which introduce buffer on both sides of main flow channel 302. Buffer introduction channels 304 and 305 hydrodynamically focus the sample in the center of main flow channel 302. This arranges the cells in the sample in substantially a single line. Alternatively, a single buffer introduction channel may be used to hydrodynamically focus the sample on one side of main flow channel 302.

Particle detector 300 also includes salt bridge chambers 321 and 322 which contain DADMAC and are in fluid communication with main flow channel 302. Electrolyte inlets 315 and 316 contain electrolyte and are in fluid communication with salt bridge chambers 311 and 312. Electrolyte inlets 315 and 316 are coupled to electrodes 325 and 326. Electrodes 325 and 326 pass through top layer 210 and may be electrically coupled to POC analyzer 100. Electrodes 325 and 326 may be made of Ag/AgCl or any other suitable material. A collection chamber 319 in fluid communication with main flow channel 302 collects the sample at the end.

Particle detector 300 may be fabricated with a standard soft lithography process. An SU-8 or silicon based mold is fabricated by photolithography with polydimethylsiloxane (PDMS). Particle detector 300 is manufactured by filling salt bridge chambers 321 and 322 with a prepolymer mixture of a photoinitiator and monomers and exposing it with UV. The prepolymer mixture is composed of 65% diallyldimethylammonium chloride aqueous solution, 2% 2-dydroxy-4'-(2-hydroxyethoxy)-2-methylpropiophenone (photoinitiator) and 2% N,N'-methylenebisacrylamide (cross-linker). After polymerization, the remaining prepolymer mixture is washed away with buffer solution (1M KCl). For the electrical measurement, KCl solution is filled into electrolyte inlets 315 and 316 connected to salt bridge chambers 321 and 322 and anions, Cl— ions in this case is flowed through salt bridge chambers 321 and 322 by applying DC bias between electrodes 325 and 326 in the KCl solution. This drives a current between salt bridge chambers 321 and 322 and the impedance between salt bridge chambers 321 and 322 is monitored while cells pass through main flow channel 302 between salt bridge chambers 321 and 322 which generates change in impedance across electrodes 325 and 326. The excitation signal may have a voltage of approximately 0.01 V to 10 V AC or DC, and a frequency of 50 Hz to 10 kHz if AC is used.

Figure 6B:
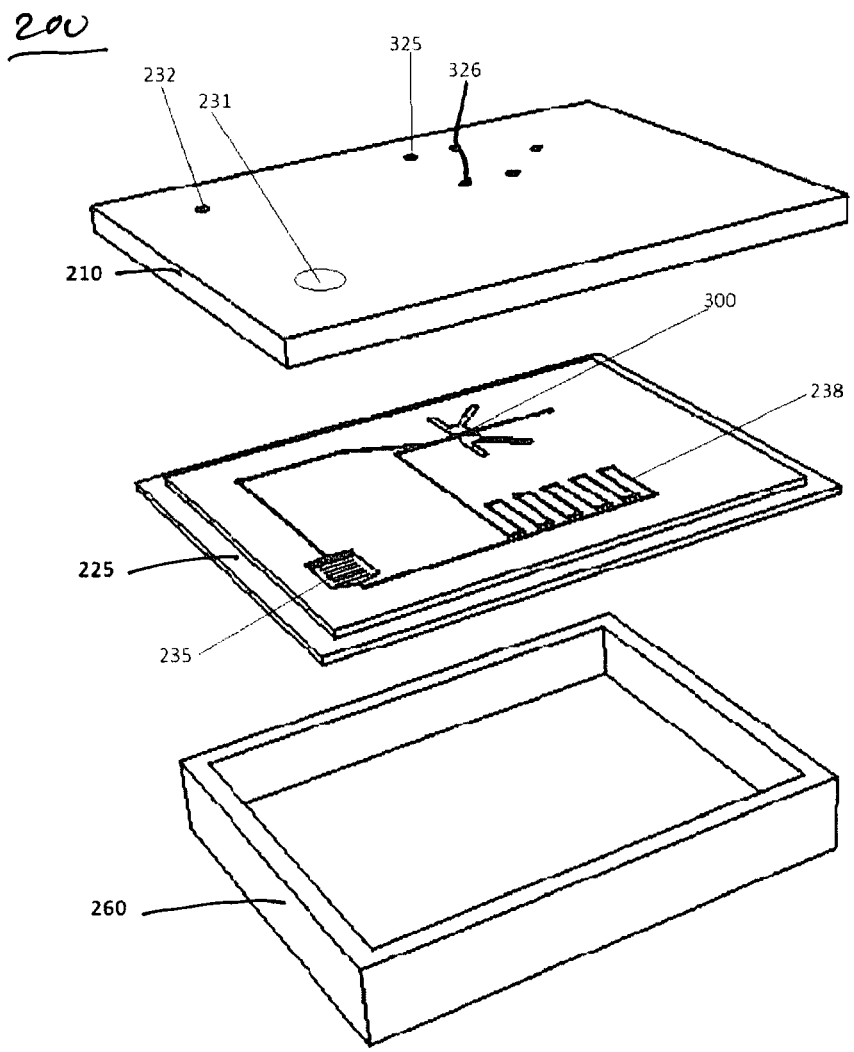
FIGS. 6A-6B show assembled and exploded views of another embodiment of a test card.
Figure 6A:
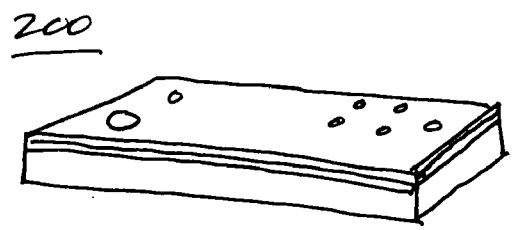

FIGS. 6A-6B show assembled and exploded views of another embodiment of test card 200. Test card 200 includes a top layer 210, a combined layer 225, and a waste layer 260. Combined layer 225 combines the elements found in particle detector layer 220 and primary separation layer 230 into a combined layer 225. Combined layer 225 includes a primary separation chamber 235, trapping channel 238, and particle detector 300. Sample inlet 231 allows a sample to be introduced into primary separation chamber 235. Buffer inlet 232 allows buffer to be introduced into primary separation chamber 235 as well as main flow channel 302.

Example 1

Circulating Tumor Cells (CTCs)

Test card 200 may be used to detect circulating tumor cells (CTCs) in whole blood. A sample of whole blood comprising plasma, platelets, red blood cells, white blood cells, and CTCs is collected with an anticoagulant and inserted into sample inlet 231. Test card 200 is then inserted into POC analyzer 100. The sample reaches primary separation chamber 235 and is introduced substantially perpendicular to filtration surface 236 by sample inlet 231. The plasma, platelets, red blood cells, and smaller white blood cells pass through pores 237 into waste chamber 260. Pores 237 may have a diameter of approximately 14-18 μm, and preferably approximately 16 μm. Larger white blood cells and CTCs are too large to pass through pores 237 and remain in primary separation chamber 235. POC analyzer 100 may apply a pressure of approximately 0-50 psi into sample inlet 231 for 1-3 minutes to facilitate the filtration process.

A buffer is introduced into the primary separation chamber 235 in a direction substantially parallel to filtration surface 236. Sample inlet 231 may be closed to prevent backflow of the buffer. Buffer enters from buffer inlet 232 substantially parallel to filtration surface 236 to create a "sweeping" action across filtration surface 236 toward trapping channel 238. Buffer inlet 232 height at the entry point into primary separation chamber 235 is reduced while length across is widened to cause spreading of buffer to cause complete sweeping of filtration surface 236 as buffer flows from buffer inlet 232 and buffer moves towards the trapping channel 238. Phosphate buffered saline or other pH buffering buffer having osmolality of about 275-299 milli-osmoles per kilogram to maintain normal cell function and volume may be used. This has the effect of "sweeping" or dislodging the white blood cells and CTCs on filtration surface 236 into trapping channel 238, especially white blood cells and CTCs that may be partially "stuck" or disposed in pores 237. Again, POC analyzer 100 is capable of applying a pressure into buffer inlet 232 to facilitate the sweeping process.

The buffer carries the unfiltered residual white blood cells and CTCs through trapping channel 238. The meandering path of trapping channel 238 increases the probability that the white blood cells will contact the walls of trapping channel 238 and bind to the walls, which have been treated with CD45 antibodies or other capture agent which specifically binds with white blood cells. The CTCs do not bind to the walls and pass through trapping channel 238.

The buffer carries the CTCs to the particle detector 300. The CTCs enter through sensor inlet 301 and into main flow channel 302. Additional buffer from buffer reservoir 303 is introduced through buffer introduction channels 304 and 305 into main flow channel 302 to hydrodynamically focus the CTCs in the center of main flow channel 302. The hydrodynamically focused CTCs pass between connection channels 313 and 314 and are counted. A voltage of approximately 5 mV to 500 mV may be applied to electrodes 325 and 326 and impedance measured by POC analyzer 100.

The CTCs collect in collection chamber 319, where they may be removed from test card 200 for further analysis, if desired.

Example 2

Transplantation Tissue Typing

Test card 200 may be used for tissue typing, where the tissues of a prospective donor and recipient are tested for compatibility prior to transplantation. An embryo can be tissue typed to ensure that the embryo implanted can be a cord-blood stem cell donor for a sick sibling.

This application uses filtration surface 236 with pores 237 having a diameter of approximately 5 μm. A small amount of white blood cells from a sample is retained in primary separation chamber 235 and move through trapping channel 238 with walls specifically treated with known anti-HLA (human leukocyte antigen) antibodies. If the antibodies recognize the epitope on the major histocompatibility complex (MHC), then the white blood cells bind to the walls of trapping channel 238 and are not counted by particle detector 300. This allows identification of a cell's MHC indirectly based on the specificity of the known antibodies present in trapping channel 238.

Example 3

Human Leukocyte Antigen (HLA) Typing for Disease Association

Test card 200 may be used to detect HLA A, B, C, which may be useful in relation to certain human disease states.

This application uses filtration surface 236 with pores 237 having a diameter of approximately 5 μm. The white blood cells in a sample are retained in primary separation chamber 235 and move through trapping channel 238 with walls treated with specific anti-HLA (human leukocyte antigen) antibodies. If the antibodies recognize the HLA antigen on the white blood cells, then the white blood bind to the walls of trapping channel 238 and are not counted by particle detector 300. This allows identification of cell's HLA indirectly based on the specificity of the known antibodies present in trapping channel 238.

Example 4

Acquired Hematopoietic Stem Cell Disorder

Test card 200 may be used to identify paroxysmal nocturnal hemoglobinuria (PNH), an acquired hematopoietic stem cell disorder in which blood cells are missing certain cell surface markers, causing some or all of body's red blood cells (RBCs) to be destroyed by a process called hemolysis. Test card 200 may be used to detect blood cells which lack a combination of the surface markers CD45, CD14, CD33, CD16, CD24, CD64, and CD15.

This application uses filtration surface 236 with pores 237 having a diameter of approximately 5 μm. Trapping channel 238 has walls treated with CD45, CD14, and/or CD33 antibodies. White blood cells affected by PNH do not bind to the walls and pass through trapping channel 238 to be counted by particle detector 300.

Figure 7A:
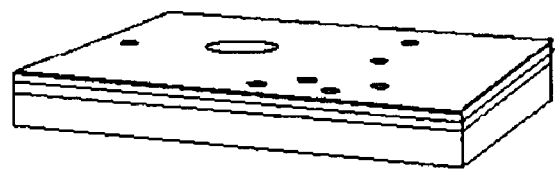
FIGS. 7A-7B show assembled and exploded views of another embodiment of a test card.
Figure 7B:
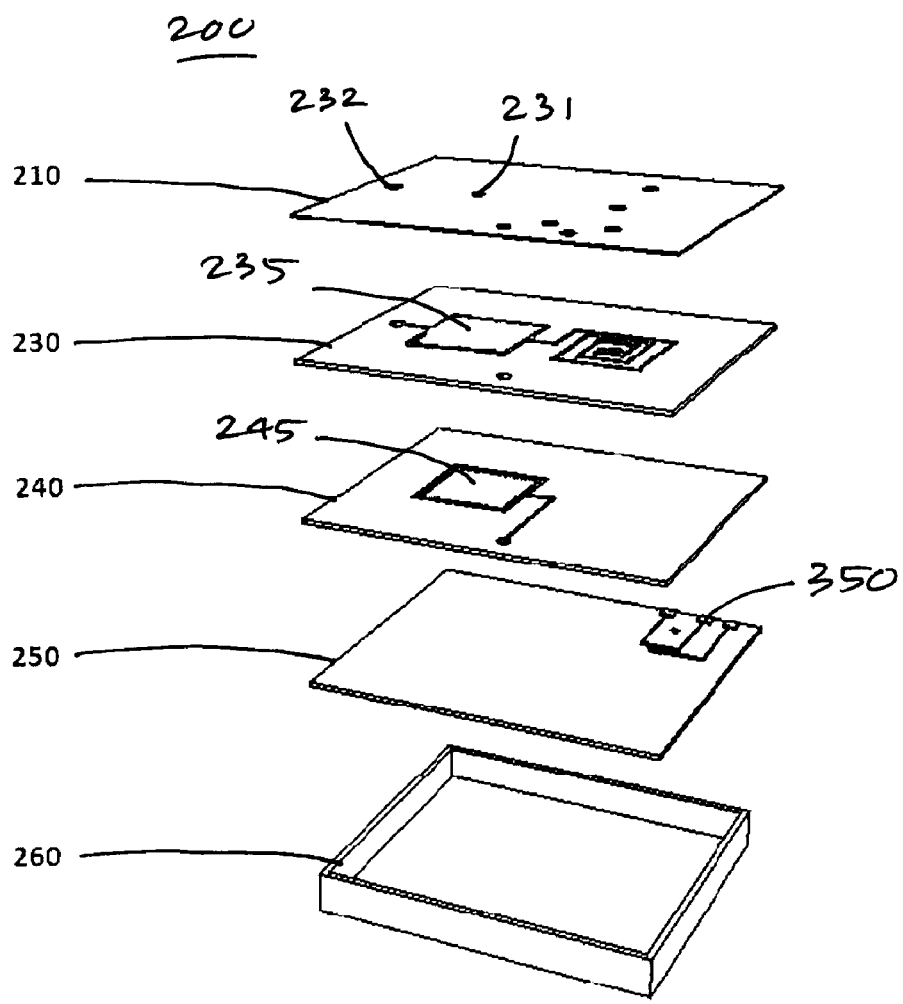

FIGS. 7A-7B show assembled and exploded views of another embodiment of test card 200. Test card 200 includes a top layer 210, a primary separation layer 230, a secondary separation layer 240, a nanowire sensor layer 250, and a waste collection layer 260.

Figure 8A:
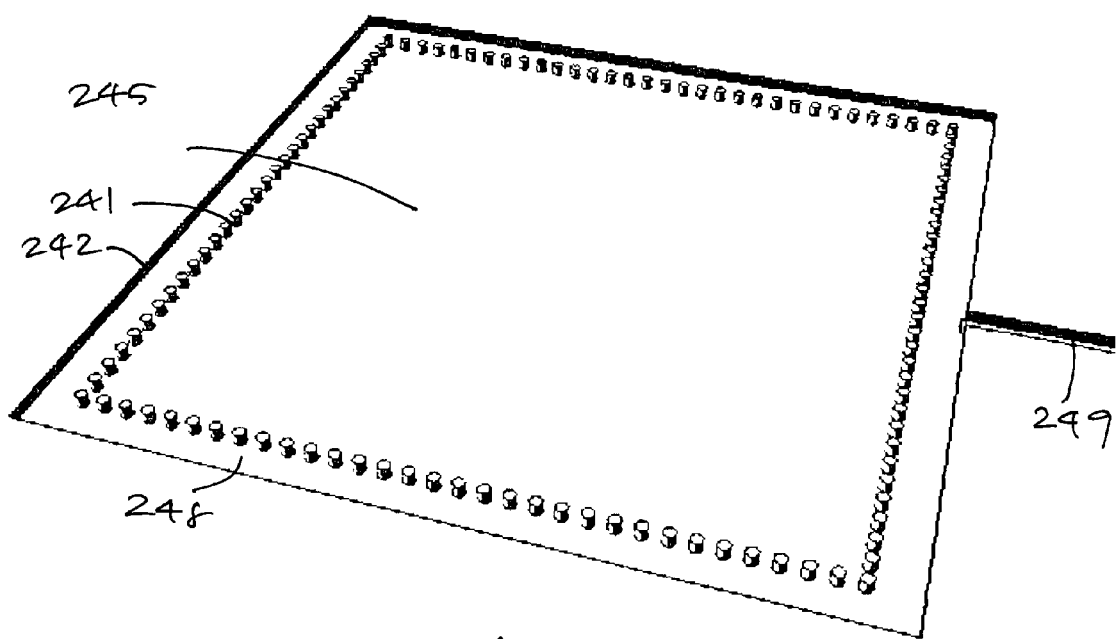
FIGS. 8A-8B shows enlarged views of the top and bottom sides, respectively, of a secondary separation layer.
Figure 8B:
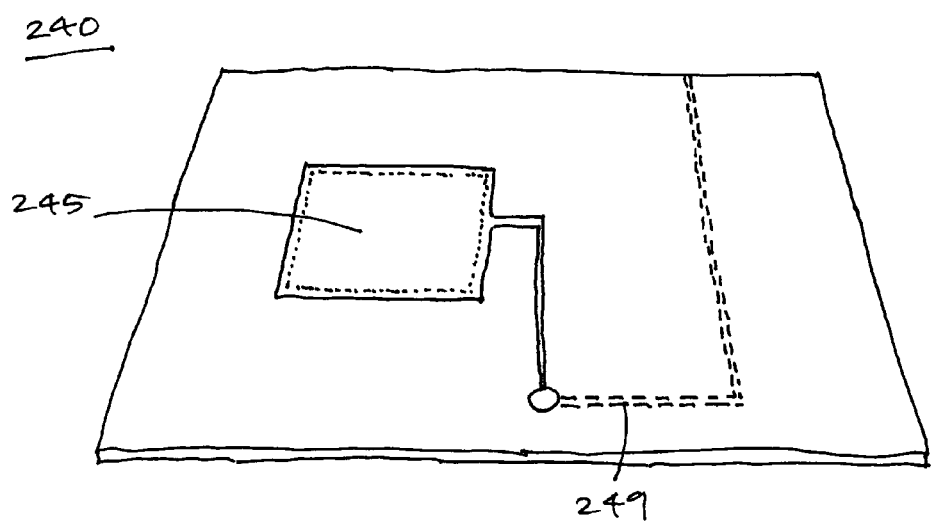

FIGS. 8A-8B shows enlarged views of secondary separation layer 240. Secondary separation layer 240 includes a secondary separation chamber 245 in fluid communication with primary separation chamber 235 through pores 237. Secondary separation chamber 245 collects plasma, red blood cells, platelets, and other blood components smaller than the size of pores 237. Secondary separation chamber 245 has an inner wall 241 and an outer wall 242. Inner wall 241 has open spacing of approximately 400 μm wide which allow particles to move out of secondary separation chamber 245 and into channel 248 between inner wall 241 and outer wall 242 of secondary separation chamber 245. The walls of channel 248 may be treated with capture agent to specifically bind particles collected in secondary separation chamber 245. The sample travels through a channel 249 which may run along the top and the bottom of secondary separation layer 240 before reaching nanowire sensor 350.

Nanowire sensor layer 250 includes a nanowire sensor 350. Nanowire sensor 350 is capable of quantifying the amount of a particular substance in the plasma or other sample.

Figure 9A:
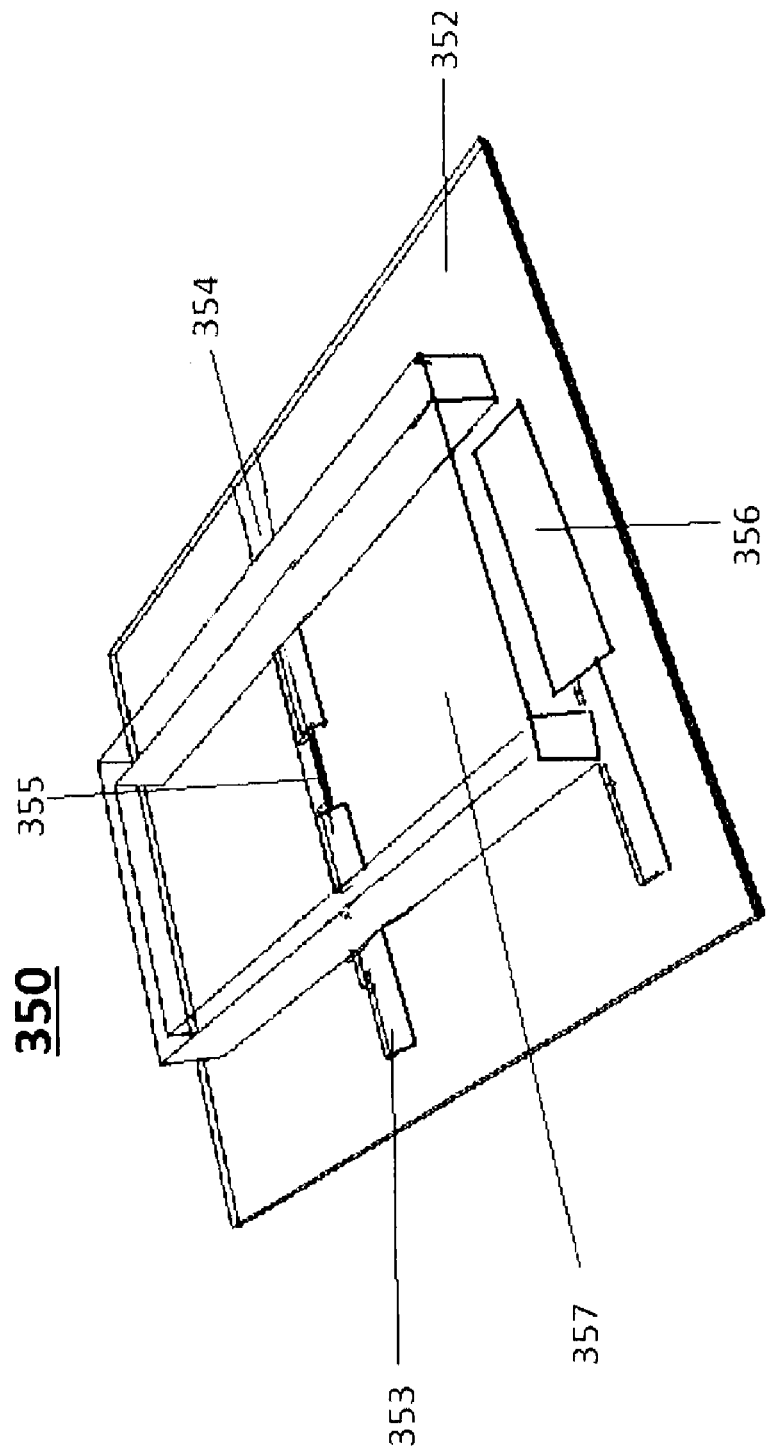
FIG. 9A shows an enlarged view of one embodiment of a nanowire sensor.

FIG. 9A shows an enlarged view of one embodiment of a nanowire sensor 350. Nanowire sensor 350 is a silicon nanowire field effect transistor (FET). Nanowire sensor 350 includes a base 352. Nanowire sensor 350 also includes a source electrode 353 and a drain electrode 354, both disposed on base 352. Source electrode 353 and drain electrode 354 may be covered with an insulating layer. Nanowire sensor 350 also includes a nanowire 355 coupled to source electrode 354 and drain electrode 354. Nanowire 355 is semiconducting and may be made of Si, Ge, InAs, ZnO, SiGe, or any other suitable material. Nanowire 355 may have a thickness of approximately 1 nm to 500 nm, and preferably approximately 20 nm. Nanowire 355 may be doped to approximately $10^{16}/cm^3$ to $10^{20}/cm^3$, and preferably approximately $10^{18}/cm^3$. Nanowire sensor 350 also includes a control electrode 356 disposed on base 352.

Nanowire sensor 350 also includes a control electrode 356. Control electrode 356 may be positioned approximately 0.01 mm to 1 mm from nanowire 355, and preferably approximately 0.1 mm. In one embodiment, control electrode 356 is made of Au, but may also be made of Ag, Cu, Zn, Cd, Fe, Ni, Co, or any other suitable material. In one embodiment, control electrode 356 is functionalized with a peptide nucleic acid (PNA) specific for a target molecule attached to control electrode 356 via a, e.g., amine, carboxylic acid, aldehyde or thiol linkage. The target molecule may be, e.g., a nucleic acid molecule containing a preselected nucleotide sequence. The PNA may include a spacer unit, e.g. an amino acid linker or a monomer or multimer of, e.g., 8-amino-3,6,-dioxaoctanoic acid, or any other suitable spacer that provides the PNA with flexibility once it is attached to control electrode 356. The signal change may be detected by measuring the gating response with the FET. An applied voltage to control electrode 356, $V_{CE}$, provides a gating input for the FET. When target molecules bind to control electrode 356, the capacitance between control electrode 356 and nanowire 355 changes, and the gating response will be different for the same $V_{CE}$. Control electrode 356 may be large, e.g., 5 μm×5 μm to 500 μm×500 μm with about 50 μm×50 μm (length×width) being preferred to increase the number of target molecules bound to control electrode 356 thereby enhancing detection sensitivity. Control electrode 356 may be any suitable thickness, e.g., about 10 nm to about 200 nm. The increased size of control electrode 356 and the functionalization of control electrode 356 rather than nanowire 355, contribute to the increased sensitivity and specificity of nanowire sensor 350.

Nanowire 355 and control electrode 356 are in fluid communication with each other. In one embodiment, nanowire 355 and control electrode 356 are placed in a microfluidic channel 357. Alternatively, nanowire 355 and control electrode 356 may be placed in a sample chamber where the sample is static or agitated. Control electrode 356 may be substantially the same width as microfluidic channel 357, or any other suitable size or width.

Control electrode 356 may be functionalized with any one of a number of cancer antigens. Control electrode 356 may be functionalized with a peptide nucleic acid (PNA) complementary to protein 53 (p53) nucleic acid (tumor suppression) or human epidermal growth factor receptor 2, HER2/neu nucleic acid or others. Control electrode 356 may be functionalized with an antibody to cancer antigens: CA27.29, carcinoembryonic antigen (CEA), CA15-3, prostate-specific antigen (PSA), or others.

Control electrode 356 may be functionalized to detect any one of a number of protein biomarkers. Control electrode 356 may be functionalized with an antibody to C reactive protein (CRP), a heart disease and stroke risk factor, an antibody to B-type natriuretic peptide (BNP) to diagnose congestive heart failure (CHF), an antibody to creatinine kinase to test for acute myocardial infarct and skeletal muscular damage, an antibody to transferrin to test for nutritional status or liver function, an antibody to homocysteine to screen patients at risk for heart disease and stroke, an antibody to small blood molecules such as glucose for diabetes testing, or an antibody to hepatitis B surface antigen (HBsAG) to test for the presence of acute infection.

Control electrode 356 may be functionalized with any one of a number of antibodies to detect immunoglobulins and antibodies for detecting certain types of cancer, disease, infection and immune status. Control electrode 356 may be functionalized with an antibody to specific immunoglobulins (IgA, IgG and IgM) to diagnose myeloma, macroglobulinemia of Waldenström, and evaluate monoclonal gammopathy and amyloidosis. Control electrode 356 may be functionalized with an antibody to anti-hepatitis B used as an indicator of clinical recovery and subsequent immunity to the hepatitis B virus, an antibody to anti-double-stranded DNA (anti-ds-DNA) to detect antibodies associated with systemic lupus erythematosus (SLE), or an antibody to allergen-specific immunoglobulin E (IgE) to diagnose atopic dermatitis, eczema, parasitic infections, allergic bronchopulmonary aspergillosis, and immunodeficiency.

Control electrode 356 may be functionalized with any one of a number of complementary peptide nucleic acids (PNAs) for detecting a wide variety of infectious diseases. Control electrode 356 may be functionalized with PNA complementary to HSV nucleic acid, hepatitis C nucleic acid, HIV-1 nucleic acid, *Pneumocystis carinii* pneumonia (PCP) nucleic acid, bacterial nucleic acid, *Legionella pneumophilia* nucleic acid, or *streptococcus* B nucleic acid.

Although the examples above describe using whole blood as samples, other samples such as urine may also be used with test card 200. For example, control electrode 356 may be functionalized with an antibody to albumin to detect albumin in urine as an early sign of diabetes.

Test card 200 is designed to have enhanced detection sensitivity and specificity compared to other nanoscale devices. Test card 200 includes a microfluidic device that separates components in the sample by size as well as by charge and a nanowire sensor 350 that detects the target biomolecule based upon the molecule's biochemical and physical properties. Also described are methods for detecting the presence or absence of one or more biomolecules in a sample and methods for diagnosing a disease state in a subject based upon the presence of the biomolecules in a sample of the subject. The methods described herein are designed to provide improved sensitivity for detecting picomolar and femtomolar amounts of nucleic acids and for detecting biomolecules in a sample.

Test card 200 includes a microfluidic device and a nanowire sensor 350. The microfluidic device includes a size exclusion mechanism for separating molecules in a sample based upon one or more of at least size, structure and charge. Nanowire sensor 350 includes a base 352 and a gated nanowire field effect transistor (NW-FET) having a predetermined current-voltage characteristic and adapted for use as a biological sensor. Nanowire sensor 350 also includes a microfluidic channel 357 having an inlet. Nanowire sensor 350 includes a source electrode 353, a drain electrode 354, a nanowire 355 connected to and disposed between source electrode 353 and drain electrode 354, and a control electrode 356 functionalized with a binding site specific for a target molecule forming an FET having a predetermined current-voltage characteristic. The NW-FET is disposed on a base, 352 and is between base 352 and microfluidic channel 357. A binding event occurring between a target molecule and a binding site on control electrode 356 causes a detectable change in the current-voltage characteristic of the NW-FET. In a preferred embodiment, nanowire 355 is a silicon based nanowire, but may also be Ge, InAs, ZnO and SiGe or any other semiconductor material. Control electrode 356 may be, e.g., a metal control electrode, e.g., Au, Ag, Cu, Zn, Cd, Fe, Ni, Co or any other suitable element or compound. Preferably control electrode 356 is Au. The binding site may be, e.g., a peptide nucleic acid (PNA), antibody, aptamer, peptide or other agents specific for a target molecule attached to control electrode 356 via a e.g., amine, carboxylic acid, aldehyde or thiol linkage (see, e.g., FIG. 9C). The target molecule may be, e.g., a nucleic acid molecule containing a preselected nucleotide sequence. The PNA may include a spacer unit, e.g. an amino acid linker or a monomer or multimer of, e.g., 8-amino-3,6,-dioxaoctanoic acid, or any other suitable spacer that provides the PNA with flexibility once it is attached to the control electrode. The signal change may be detected by measuring the gating response with the NW-FET. An applied voltage to control electrode 356, $V_{CE}$, provides a gating input for the NW-FET. When target molecules bind to control electrode 356, the capacitance between the control electrode and nanowire 355 changes, and the gating response will be different for the same $V_{CE}$. Control electrode 356 may be large, e.g., 5 μm×5 μm to 500 μm×500 μm with about 50 μm×50 μm (length×width) being preferred to increase the number of target molecules bound to control electrode 356 thereby enhancing detection sensitivity Control electrode 356 may be any suitable thickness, e.g., about 10 μm to about 200 μm. The increased size of control electrode 356 and the functionalization of control electrode 356 rather than nanowire 355, contribute to the increased sensitivity and specificity of nanowire sensor 355.

Another embodiment of this invention is a method for detecting the presence or absence of a target nucleic acid molecule in a sample, particularly a biological sample, by applying the sample to nanowire sensor 350, and detecting a signal change nanowire sensor 350, wherein the signal change is induced by the binding of a target molecule in the sample to the binding site on control electrode 356 in nanowire sensor 350. The sample may be a biological sample, e.g., a blood or plasma sample. The target molecule is preferably a DNA molecule containing a preselected sequence, e.g., a sequence of a tumor-derived DNA that is characteristic of the presence of the tumor. The tumor-derived DNA may be a marker or a potential marker serving as a diagnostic and prognostic indicator of presence of the tumor and its progression and predictive indicator or response to therapy. The DNA may be, for example, a mutant K-ras and the tumor may be pancreatic cancer, particularly pancreatic adenocarcinoma.

The method is also useful for establishing a correlation between the concentration of a target DNA in the biological sample and cancer status. The method may also be used as a screening method for early detection of the tumor from which the target DNA is derived or for assaying the progression of the tumor. For example, the method can be used to detect a change from a non-cancerous pancreatic lesion to a cancerous pancreatic lesion, by assaying a sample for a subject having pancreatic lesions for the presence of an additional mutated K-ras in a sample from the subject, or assaying a sample from the subject for the presence of an elevated level of a mutant K-ras DNAs that is above a clinically significant mutant K-ras DNA level. The presence of additional mutant K-ras DNAs or an elevation in mutant K-ras DNA in the subject's sample is an indication that the pancreatic lesions are, or will become, cancerous. Additionally, the method is useful for predicting a response to therapy or selecting patients who would be most appropriately treated with particular therapy. For example, as presented at the American Society of Clinical Oncology and European Society of Medical Oncology in 2008, the presence of K-ras mutations in metastatic colorectal cancer was associated with generally poor response to antibodies directed at the epidermal growth factor receptor (EGFR) kinase, such as Cetuximab (Erbitux, Imclone, Inc.) and Panitumumab (Vectibix, Amgen Inc.)

A further embodiment of this invention is a method for detecting a pre-selected DNA sequence in genomic DNA isolated from a tissue sample. The genomic DNA sample is contacted with control electrode 356 in nanowire sensor 350, wherein control electrode 356 is functionalized with a binding site specific for the pre-selected DNA, and a change in the conductivity or current is detected. The pre-selected DNA sequence may be e.g., a DNA sequence specific to a virus, e.g., a hepatitis B virus, a human immunodeficiency virus, a human papilloma virus, or a cytomegalovirus.

A field effect transistor (FET) is a three-electrode device including a gate electrode, a source electrode and a drain electrode. FETs are described in more detail in The Art of Electronics, Second Edition by Paul Horowitz and Winfield Hill, Cambridge University Press, 1989, pp. 113-174, the entire contents of which is hereby incorporated by reference. This availability of charge carriers is controlled by a voltage applied to a third "control electrode" also known as the gate electrode. The conduction in the channel is controlled by a voltage applied to the gate electrode, which produces an electric field across the channel.

The sensing device includes (a) nanowire 355, which is connected to and disposed between a source electrode 353 and a drain electrode 354, (b) a gate electrode or control electrode 356, and (c) a microfluidic channel 357, optionally having a fluid inlet and outlet. Source electrode 353, drain electrode 354, nanowire 355 and control electrode 356 form nanowire sensor 350. Nanowire 355 and control electrode 356 are physically separate and control electrode 356 is in the flow of microfluidic channel 357. Nanowire sensor 350 and microfluidic channel 357 are disposed on a supporting base 352. Nanowire sensor 350 is located between base 352 and microfluidic channel 357. Control electrode 356 is functionalized with binding sites for a preselected target molecule. A target molecule binding to the binding site on control electrode 356 provides the voltage at the gate which produces the electric field which changes the carrier distribution of nanowire 355. This change in carrier distribution in nanowire 355 affects the flow of current through nanowire 355 which may be detected by a detector, e.g. I-V scanning with a voltmeter.

Because the measurements are performed in a solution phase, source electrode 353 and drain electrode 354 attached to nanowire 355 are protected from exposure to the sample in microfluidic channel 357 by coating source electrode 353 and drain electrode 354 with an insulating material. Various insulating materials are available, e.g., silicon nitride, silicon oxide and any other suitable material. Silicon nitride or silicon oxide may be deposited on source electrode 353 and drain electrode 354 by plasma-enhanced chemical vapor deposition (PECVD) to provide the insulation. The conditions for thin layer deposition silicon nitride or silicon oxide using PECVD may be further optimized.

Nanowire sensor 350 may also include a device for measuring a change in the capacitance or other property of control electrode 356. Nanowire sensor 350 is operated with simple electronics, preferably, a micron size source electrode 353, defined by photolithography that is connected to nanowire 355 and other electrical components, e.g., a power supply, an amplifier, and a voltmeter. In order to minimize the parasitic current through the electrolyte containing sample in microfluidic channel 357, source electrode 353 and drain electrode 354 are isolated with an insulating material such as silicon nitride or silicon dioxide. Control electrode 356 is in the flow of microfluidic channel 357. Owing to the small size of microfluidic channel 357, only a small volume of the sample (typically less than one milliliter) will be required. The sample solution flows through microfluidic channel 357 at a fixed flow rate either by gravity or by pumping through microfluidic channel 357. The sample may be pumped through by a syringe pump, a peristaltic pump, or any other suitable device. The sample may also be forced to flow through microfluidic channel 357 using a compressed air or nitrogen regulator. The sample may be pumped through at a rate of approximately 1 to 100 μl/min.

As used herein, the term "nanowire" is as described in U.S. Pat. No. 7,385,267 incorporated in its entirety herein, which defines a nanowire as an elongated nanoscale semiconductor at any point along its length, has at least one cross-sectional dimension and, in some embodiments, two orthogonal cross-sectional dimensions less than 500 nm, preferably less than 200 nm, more preferably less than 150 nm, still more preferably less than 100 nm, even more preferably less than 70 nm, still more preferably less than 50 nm, even more preferably less than 20 nm, still more preferably less than 10 nm, and even less than 5 nm. In other embodiments, the cross-sectional dimension can be less than 2 nm or 1 nm. In one set of embodiments, the nanowire has at least one cross-sectional dimension ranging from 0.5 nm to 200 nm. Where nanowires have a core and an outer region, the above dimensions relate to those of the core. The cross-section of the elongated semiconductor may have any arbitrary shape, including, but not limited to, circular, square, rectangular, elliptical and tubular. Regular and irregular shapes are included. A non-limiting list of examples of materials from which nanowires of the invention can be made appears below. Nanotubes are a class of nanowires that may be used in the invention and, in one embodiment, devices of the invention include wires of scale commensurate with nanotubes. As used herein, a "nanotube" is a nanowire that has a hollowed-out core, and includes those nanotubes know to those of ordinary skill in the art. A "non-nanotube nanowire" is any nanowire that is not a nanotube. In one set of embodiments of the invention, a non-nanotube nanowire having an unmodified surface (not including an auxiliary reaction entity not inherent in the nanotube in the environment in which it is positioned) is used in any arrangement of the invention described herein in which a nanowire or nanotube can be used. A "wire" generally refers to any material having a conductivity at least that of a semiconductor or metal. For example, the term "electrically conductive" or a "conductor" or an "electrical conductor" when used with reference to a "conducting" wire or a nanowire refers to the ability of that wire to pass charge through itself Preferred electrically conductive materials have a resistivity lower than about $10^{-3}$, more preferably lower than about $10^{-4}$, and most preferably lower than about $10^{-6}$ or $10^{-7}$ Ωm.

Nanowires 355 may include carbon nanotubes, nanorods, nanowires, organic and inorganic conductive and semiconducting polymers, and the like unless otherwise specified. Other conductive or semiconducting elements that may not be molecular wires, but are of various small nanoscopic-scale dimension, also can be used in some instances, e.g., inorganic structures such as main group and metal atom-based wire-like silicon, transition metal-containing wires, gallium arsenide, gallium nitride, indium phosphide, germanium, cadmium selenide structures, or any other suitable composition. A wide variety of these and other nanowires can be grown on and/or applied to surfaces in patterns useful for electronic devices in a manner similar to techniques described herein involving nanowires, without undue experimentation. Nanowires 355 should be able to be formed of at least 1 μm, preferably at least 3 μm, more preferably at least 5 μm, and more preferably still at least 10 or 20 μm in length, and preferably are less than about 100 nm, more preferably less than about 75 nm, and more preferably less than about 50 nm, and more preferably still less than about 25 nm in thickness (height and width). Nanowires 355 should have an aspect ratio (length to thickness) of at least about 2:1, preferably greater than about 10:1, and more preferably greater than about 1000:1.

Preferably nanowire 355 is a silicon nanowire (SiNW), preferably a silicon non-nanotube (solid) nanowire. However, any suitable material may be used.

Various methods are available in the art for producing nanowire 355 see e.g., U.S. Pat. No. 7,301,199 and U.S. Pat. No. 7,410,904 incorporated herein in their entirety by reference. Methods such as the "bottom-up" method are available, which is the growing of nanowires as bulk materials by the vapor-liquid-solid (VLS) technique. This method produces high quality nanowires, but it is difficult to make homogeneous nanowires in terms of lengths and diameters. Also, it is difficult to position the nanowire on the expected spots and to align it with other components of nanowire sensor 350 including electrodes, which leads to low device-to-device uniformity (Gao et al. Anal Chem 2007; 79:3291-7). Other methods that may be used are the "top-down" techniques based on e-beam lithography and wet/dry etching. These latter methods are preferred as they provide more controllability over the size and the location of nanowires, which enables high throughput and automation for production.

In various embodiments, any number of different methods may be employed to fabricate control electrode 356 including examples and combinations of the following: imprinting, lithography, chemical vapor deposition (CVD), etching, laser ablation, arc discharge, and/or electrochemical methods. Control electrode 356 may have dimensions of 5 μm×5 μm to 500 μm×500 μm dimensions, preferably about 50 μm×50 μm (length×width), or any other suitable dimension. Control electrode 356 may be any suitable thickness, e.g., about 10 μm to about 200 μm.

The process of coating control electrode 356 with a "functional agent" may be referred to herein as "functionalization" and the coated control electrode as "functionalized." Functional agents may, for example, bind specific chemical and/or biological species of interest, such as, for example, thiol groups, nucleic acids, e.g., deoxyribonucleic acid or "DNA", peptide nucleic acids or "PNA", and ribonucleic acid or "RNA", aptamers, hormones, carbohydrates, proteins, antibodies, antigens, molecular receptors, and/or cellular surface binding sites, to provide a few biochemical examples. In this invention, the functional agent bound to control electrode 356 to form the binding site is specific for, or complementary to, a target molecule in a sample. For example, a first electrode-posited gold functional agent may be, or bind to, a thiol-terminated PNA functional agent that may, in turn, bind a complementary DNA target molecule in a sample being assayed. Control electrode 356 may be bound to about 0.1 μm to about 100 μm, preferably about 1 μm to about 10 μm PNA.

The SiNW and a non-metal control electrode 356 may be doped with either p-type or n-type dopants. The surface of control electrode 356 may be modified with capture agent, a PNA containing a sequence that is complementary to a preselected DNA sequence, e.g., a K-ras mutation ssDNA.

Nanowire 355 or control electrode 356 or both may be doped. Two different methods, spin-on dopants based doping and ion implantation, may be used to dope nanowire 355 and/or control electrode 356 for further optimization. For the spin-on dopants method, a substrate is spin coated with p-type or n-type spin-on dopant solution followed by a diffusion process at high temperature. The final doping level may be decided by the temperature and the time of the thermal process. For ion implantation, high-energy ions such as boron, phosphorus, or arsenic are produced from various gas sources in an accelerator and are directed onto the substrate. Ions are injected into the near-surface region of the substrate. Both methods have been reported to give good results (Gao et al. Anal Chem 2007; 79:3291-7, and Wang et al., Nano Lett 2006; 6(6):1096-1100). The optimal doping level may be chosen based on four point probe measurements (see, e.g., Robert F. Pierret, 'Semiconductor Device Fundamentals,' Addison Wesley, Chapter 3, pp. 85-89 and section 3.1.4 and Sato et al. Journal of Surface Analysis 11(2)58-61 (2004) both incorporated herein in their entirety by reference). A doping level of about $10^{18}$ holes or donor atoms/$cm^3$ may be used as a starting point for the optimization. The doping level may be increased or decreased as needed.

Synthetic peptide nucleic acid oligomers (PNAs) may be obtained commercially from a number of sources. In this invention PNAs may be bound to control electrode 356 to form the binding site. The PNA is specific/complementary to a pre-selected nucleotide sequence in a target molecule in a sample, e.g., DNA or RNA, preferably a ssDNA. Preferably the PNAs used in this invention are of a suitable length and sequence to specifically bind a target DNA present in a sample, e.g., about 5 to about 75, preferably about 20 to about 50 nucleotides, and are 80%, 85%, 90%, 95%, 99% or 100% complementary to a pre-selected sequence in a target DNA. Preferably the sequence of the PNA is 100% complementary to the pre-selected sequence. The PNA may comprise a sequence that is the complement or anyone of SEQ ID NO: 2, 3, 4, 5, or 6. Preferably, the target DNA is hybridized to the PNA attached to control electrode 356 under conditions suitable for detecting a single base pair mismatch between the preselected sequence of the target DNA and the PNA attached to control electrode 356. Preferably the conditions are low salt hybridization conditions, e.g., 10 mM Tris HCl, pH 8.0, or equivalent conditions.

More than one nanowire sensor 350 may be used, each sensor designed to detect a different target molecule in a sample. The sensing device may also comprise more than one NW-FET, each one designed to detect a different target molecule. For example, a sensing device may comprise a plurality of NW-FETs as described herein, each one including a control electrode 356 functionalized with a binding site for a target molecule containing one of the sequences SEQ ID NO: 2-6.

The term "sample" is as described in U.S. Pat. No. 7,385, 267, which is incorporated herein in its entirety by reference, and refers to any cell, cell culture medium, tissue, or fluid from a biological source (a "biological sample"), or any other medium, biological or non-biological, that can be evaluated in accordance with the invention including, e.g., plasma, serum or water. A sample includes, but is not limited to, a biological sample drawn from an organism (e.g., a human, a non-human mammal, an invertebrate, a plant, a fungus, an algae, a bacteria, a virus, etc.), a sample drawn from food designed for human consumption, a sample including food designed for animal consumption such as livestock feed, milk, an organ donation sample, a sample of blood destined for a blood supply, a sample from a water supply, or the like. One example of a sample is a sample drawn from a human or animal to determine the presence or absence of a specific nucleic acid sequence.

The preferred sample is a blood, plasma, or serum sample, preferably a blood, plasma, or serum sample from a subject having or suspected of having a tumor, such as a pancreatic tumor. The sample may be a tissue sample homogenized and put in solution.

Nanowire sensor 350 may be manufactured as follows:

PNA immobilization on electrode: Immobilization may be characterized by X-ray photoelectron spectroscopy (XPS). XPS is an ex-situ method to evaluate chemical as well as structural properties of thin film. Quantitative analysis on the surface after HS-ssPNA immobilization may also be determined. Change of the surface coverage is monitored for HS-ssPNA monolayer and mixed self-assembled PNA monolayers containing blocking agents (mercaptoethanol). Fourier-transform infrared (FTIR) spectroscopy provides additional information about molecular fingerprints and orientation. Based on those two methods, the surface status may be determined in terms of PNA orientation as well as coverage.

Formation of the insulating layer: Because the measurement will be performed in a solution phase, the metal electrodes are protected from being exposed to the liquid. Silicon nitride and silicon oxide are most common materials for that purpose. Thin layer deposition with, e.g., PECVD will be optimized. A bi-layer lift-off method is used to form a patterned insulating layer. The underlayer is spin-coated followed by photoresist. Under the same exposure and developing condition, the underlayer developed more easily and faster than the photoresist. Suspended photoresist patterns which will act as a mask during the metal deposition step are formed to provide space around the newly formed metal patterns on the substrate after metal deposition. After the PECVD process, which forms thin layer anisotropically followed by lift-off, the metal electrode pattern is covered with silicon nitride or silicon oxide.

Doping process: At least two different doping methods are suitable: spin-on dopant method and ion implantation. After the doping, the estimated doping level is calculated by the four-point probe measurement. The sheet resistance $\rho s$ of the layer is measured. The four probes are arranged in a linear fashion. A fixed current is supplied to the outer two probes while voltage to maintain the fixed current is measured from the two inner probes. From the relationship between the current and voltage values, the sheet resistance is calculated. The doping level is calculated from the resistivity versus dopant density curve. Initial aim for the doping level will be $10^{18}/cm^3$. The aiming doping level is adjusted based on the gating performance of the NW-FET from the back gating measurement.

Nanowire FET device: E-beam lithography and various etching techniques may be used to generate the nanowire fabrication. After nanowire fabrication, it is characterized by imaging with a scanning electron microscope (SEM). Then metal electrodes are defined by, e.g., e-beam lithography, photolithography, and lift-off method. Again, the size and quality of the pattern is monitored with, e.g., an SEM. The electrical performance of the device is tested with I-V measurement and back-gating measurement. Doping level can be changed based on the gating performance.

Insulating layer: The full coverage of the metal electrodes may be confirmed by e.g., SEM imaging. Electrical isolation may be checked by, e.g., I-V measurements in liquid as well.

Example 5

Target Molecules

There are 4 significant K-ras point mutations (#1-4 below) associated with pancreatic cancer. An additional point mutation (#5 below) occurs extremely low in frequency in pancreatic cancer. Target oligonucleotides contain at least about 20-50 nucleotides of the nucleic acid sequences for K-ras and contain at least one of the four mutations (#1-4). A target oligonucleotide that contains at least about 20-50 nucleotides of the nucleic acid sequence for K-ras and containing the #5 mutation, serves as a negative control to increase the specificity for pancreatic cancer detection.

Complementary PNAs for each of the mutations #1-5 listed below and containing about 20-50 nucleotides are also synthesized. All the synthetic oligonucleotides may be purchased from a commercial source.
K-RAS CODING SEQUENCE (1-60, WILDTYPE):

(SEQ ID NO: 1)
ATG ACT GAA TAT AAA CTT GTG GTA GTT GGA GCT GGT

GGC GTA GGC AAG AGT GCC TTG ACG

| K-RAS CODING SEQUENCE (1-60, MUTATIONS #1-5) | | | | | |
|---|---|---|---|---|---|
| # | Coding Sequence Mutation | Amino Acid Mutation | Pancreatic (N) | Large Intestine (N) | Lung (N) | Bilary Tract (N) |
| 1 | c.34G > C (Substitution) | p.G12A | 338 | 57 | 48 | 21 |
| 2 | c.35G > A (Substitution) | p.G12D | 1340 | 1752 | 270 | 228 |
| 3 | c.35G > T (Substitution) | p.G12V | 829 | 1085 | 357 | 87 |
| 4 | c.34G > T (Substitution) | p.G12C | 94 | 422 | 735 | 37 |
| 5 | c.38G > A (Substitution) | p.G13D | <18 | 738 | 36 | <18 |

1: ATG ACT GAA TAT AAA CTT GTG GTA GTT GGA GCT CGT GGC GTA GGC AAG AGT GCC TTG ACG (SEQ ID NO: 2)
2: ATG ACT GAA TAT AAA CTT GTG GTA GTT GGA GCT GAT GGC GTA GGC AAG AGT GCC TTG ACG (SEQ ID NO: 3)
3: ATG ACT GAA TAT AAA CTT GTG GTA GTT GGA GCT GTT GGC GTA GGC AAG AGT GCC TTG ACG (SEQ ID NO: 4)
4: ATG ACT GAA TAT AAA CTT GTG GTA GTT GGA GCT TGT GGC GTA GGC AAG AGT GCC TTG ACG (SEQ ID NO: 5)
5: ATG ACT GAA TAT AAA CTT GTG GTA GTT GGA GCT GGT GAC GTA GGC AAG AGT GCC TTG ACG (SEQ ID NO: 6)

Peptide Nucleic Acid (PNA) Immobilization Strategy:

It has shown that PNA can detect DNA with a single base sensitivity (Wang et al., J. Amer Chem Soc 1996; 118(33): 7667-7670) and that ordered self-assembled monolayers (SAMs) of single-stranded PNA molecules on gold surfaces display specific recognition of complementary ssDNA (Briones et al., Physical Review Letters 2004; 93(20):208103). PNA is used herein as a binding site due to its high binding affinity to DNA. The PNA is immobilized onto the surface of control electrode 356, using thiol-based immobilization to form a monolayer, essentially as described by Briones et al., Phys. Rev. Lett. 93, 208103 (2004) incorporated herein in its entirety by reference. The conditions for forming the monolayer are optimized based on the PNA concentration, the length of the spacer and the thiol solution used to block the surface of the control electrode after PNA immobilization, e.g.:

The PNA concentration is optimized to form a reasonably packed monolayer, e.g., about 0.1 μm to about 10 μm: A too high concentration of PNA can completely cover the gold surface and lower the binding efficiency due to the steric effect.

Spacer Effect: The characteristics of binding on a nanosurface is very different from that in a bulk solution. A spacer of 8-amino-3,6,-dioxaoctanoic acid, which reduces the wall effect for the binding and gives more flexibility for the PNAs, is included in the PNA and multimers. e.g., dimers and trimers of 8-amino-3,6,-dioxaoctanoic acid are used to determine the optimized length of the spacer for use in the binding assay.

Effect of blocking thiol solution: To block the gold surface of the control electrode after the thiol-PNA immobilization for the successful subsequent DNA hybridization, a mercaptoethanol solution is used as a blocking agent. FIG. 9C shows the schematic representation of mixed SAM of PNA and mercaptoethanol.

Design of the Microfluidic Device and Process

Starting Sample and Sample Processing:

The sample is added to the microfluidic device and plasma is separated from blood cells and platelets by approximately 1 μm size pores 237 and enters secondary separation chamber 245.

The sample flows, or is pumped, into channel 248 which has silicon or glass conjugated to the walls of channel 248. Sufficient saturated chaotropic agent (e.g. NaI and guanidium chloride reagents) is mixed with the sample and the sample contacts channel 248 for a sufficient time and temperature to allow DNA to bind to the glass surface, approximately 5 minutes at 25° C.; the binding condition and time may be further optimized. The adsorption of DNA to the surface of glass or silica in the presence of chaotropic salts was first described by Vogelstein and Gillespie (Vogelstein et al., Proc Natl Acad Sci USA 1979; 76(2):615-619) in their work on purifying DNA fragments from agarose by glass powder.

The microfluidic channel with bound DNA is washed with mixture of 50% ethanol and 50% buffer (20 mM Tris-HCl, pH 7.2, 0.2 M NaCl, 2 mM EDTA) to remove the NaI. The DNA is then eluted from the silicon or glass surface with deionized water or low salt elution buffer. The salt and pH of the elution buffer, which carries the target DNA to the sensing device, are adjusted to, e.g., 10 mM Tris HCl, pH 8.0 to be suitable for hybridization of the target DNA to the PNA bound to the control electrode. The salt and pH adjusted hybridization solution carrying the eluted DNA flows, or is pumped, through microfluidic channel 357 to nanowire sensor 350 where it contacts control electrode 356 functionalized with peptide nucleic acid molecules that are specific for pre-selected target molecules and the target DNA hybridizes to the PNA.

Silicon Nanowire Based Sensor Design/Development

Nanowire 355 and control electrode 356, which binds the target molecules, of the sensing device of this invention are physically separate. A schematic of an embodiment of nanowire sensor 350 is shown in FIG. 9A. As illustrated, nanowire sensor 350 is operated by two components: nanowire 355, disposed between source electrode 353 and drain electrode 354, and control electrode 356. The target molecules hybridize to the PNAs bound to the surface of control electrode 356 under appropriate hybridization conditions. The SiNW-FET detects the capacitance change between control electrode 356 and nanowire 355 surface by a changed gating response. A voltage $V_{CE}$ is applied to control electrode 356, and an ionic double layer on nanowire 355 is formed by migrating ions. This phenomenon acts as a gate voltage and induces the change of charge density within nanowire 355. When the DNA target molecule binds to control electrode 356 binding sites, the capacitance between control electrode 356 and nanowire 355 is changed and the gating response from nanowire 355 is changed as well for the same $V_{CE}$. The change is detected by measuring the conductivity through nanowire 355, e.g., by monitoring the current with a voltmeter.

Figure 9B:
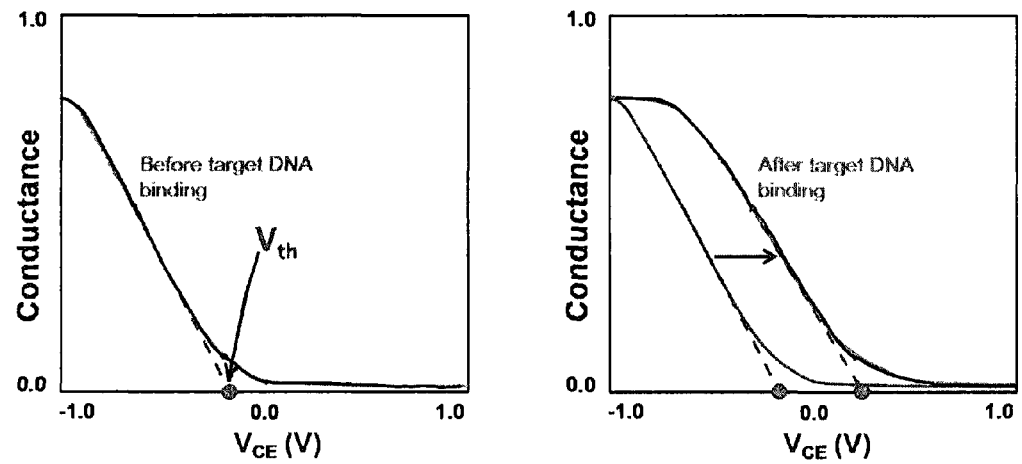
FIG. 9B shows a schematic response of a nanowire sensor.
Figure 9C:
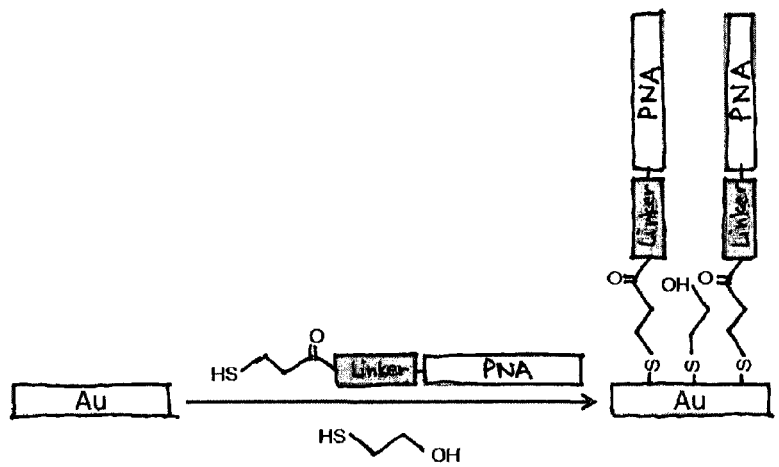
FIG. 9C shows the schematic representation of a mixed self-assembled Monolayer (SAM) of peptide nucleic acid (PNA) and mercaptoethanol.

FIG. 9B shows a schematic response of nanowire sensor 350, conductance versus control electrode voltage. The threshold voltage; $V_{th}$, is set based on linear extrapolation to zero of the linear region of conductance. When target molecules (ssDNAs) bind to the surface of control electrode 356, the capacitance between the control electrode 356 and nanowire 355 surface is changed. This capacitance change shifts the threshold voltage of nanowire 355, which is an output signal of nanowire sensor 350.

Differential Detection Schemes

To detect a point mutation in a K-ras gene, a blood sample is assayed for DNA containing a single base mutation.

A human blood sample, which is composed of many biological components, is collected and combined with an anticoagulant (e.g. EDTA, citrate, heparin). EDTA anticoagulated blood is preferred. The anticoagulated blood sample is collected and passed through the size exclusion mechanism of the microfluidic device and the DNA is separated from non-DNA molecules in the sample by binding the DNA to the microfluidic channel and then eluting the bound DNA as described above. The sample containing the eluted DNA is applied to two nanowire sensors 350: a first nanowire sensor 350 with bound PNA specific for the target nucleic acid molecule (the sample nanowire sensor 350), and a second nanowire sensor 350 which does not comprise a bound PNA for the target nucleic acid molecule (the control nanowire sensor 350), under conditions in which the target DNA in the sample hybridizes to the PNA. Signals other than the target DNA in the blood samples, which affect both sensing devices in a similar way, are eliminated by taking differential response from the two nanowire sensors 350 in the nanoscale (subtracting the signal of the control nanowire sensor 350 from that of the sample nanowire sensor 350).

Differential Detection and Two NW-FET in One Nanowire Sensor:

A disposable single-use test cartridge device is prepared including at least 2 sets of SiNW-FETs and control electrodes 356: one set consists of a first SiNW-FET and a first control electrode 356 functionalized with capture-PNAs and second set is a second SiNW FET and a second control electrode 356 without capture-PNAs. Additional sets are additional SiNW-FET and control electrodes 356 functionalized with different capture-PNAs. SiNW-FET is the same on both set (having similar performance in terms of 1-V characteristics and gating response). The device includes at least two microfluidic channels sharing the same inlet. Each channel contains one SiNW-FET. The eluted DNA sample flows into the microfluidic channels and the signals from SiNW-FETs that are positioned in each channel are detected with a detecting means and compared.

Other aspects of the invention will be clear to the skilled artisan and need not be reiterated herein. The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. A device for quantifying an amount of a particular substance in a sample, the device comprising:
   a test chamber configured to contain the sample;
   a source electrode;
   a drain electrode, the drain electrode having a lower potential than the source electrode;
   a semiconducting nanowire at least partially positioned within the test chamber, the semiconducting nanowire being coupled to the source electrode and the drain electrode;
   a detector for measuring an amount of current flowing through the nanowire; and
   a control electrode, at least partially positioned within the test chamber, in fluid communication with the semiconducting nanowire, wherein at least a portion of a surface of the control electrode is treated with a capture agent which selectively binds to the substance;
   wherein the amount of current flowing through the nanowire corresponds to a voltage applied to the control electrode, and is affected by an amount of the substance which has bound to the control electrode.

2. The device of claim 1, wherein the nanowire has a width of about 1 nm to 0.99 μm.

3. The device of claim 1, wherein the nanowire is doped to a level of approximately $10^{16}$ to $10^{20}$ holes or donor atoms/cm$^3$.

4. The device of claim 1, wherein the control electrode has a length and width of approximately 5 μm by 5 μm to about 500 μm by 500 μm.

5. The device of claim 1, wherein the control electrode has a thickness of approximately 10 nm to 200 nm.

6. The device of claim 1, wherein the capture agent is a peptide nucleic acid (PNA), an antibody, an aptamer, or a small peptide which will bind with a biomolecule.

7. The device of claim 1, wherein the capture agent on the control electrode forms a layer having a thickness of approximately 0.1 nm to 100 nm.

8. A device for quantifying an amount of a particular substance in a sample, the device comprising:
- a base;
- a source electrode coupled to the base;
- a drain electrode coupled to the base, the drain electrode having a lower potential than the source electrode;
- a semiconducting nanowire coupled to the source electrode and the drain electrode and contacting the sample; and
- a control electrode coupled to the base and contacting the sample, wherein at least a portion of a surface of the control electrode is treated with a capture agent which selectively binds to the substance;
- wherein an amount of current flowing through the nanowire corresponds to a voltage applied to the control electrode, and is affected by an amount of the substance which has bound to the control electrode.

9. The device of claim 8, wherein the nanowire has a width of about 1 nm to 0.99 μm.

10. The device of claim 8, wherein the nanowire is doped to a level of approximately $10^{16}$ to $10^{20}$ holes or donor atoms/$cm^3$.

11. The device of claim 8, wherein the control electrode has a length and width of approximately 5 μm by 5 μm to about 500 μm by 500 μm.

12. The device of claim 8, wherein the control electrode has a thickness of approximately 10 nm to 200 nm.

13. The device of claim 8, wherein the capture agent is a peptide nucleic acid (PNA), an antibody, an aptamer, or a small peptide which will bind with a biomolecule.

14. The device of claim 8, wherein the capture agent on the control electrode forms a layer having a thickness of approximately 0.1 nm to 100 nm.

* * * * *